(12) United States Patent
Landry et al.

(10) Patent No.: US 12,714,851 B1
(45) Date of Patent: Aug. 25, 2026

(54) SYSTEMS, DEVICES, AND METHODS FOR INSERTING ARRAYS

(71) Applicant: Paradromics, Inc., Austin, TX (US)

(72) Inventors: Michael E. Landry, Austin, TX (US); James Burrows, Marble Falls, TX (US); Robert James Jones, Lago Vista, TX (US)

(73) Assignee: Paradromics, Inc., Austin, TX (US)

( * ) Notice: Subject to any disclaimer, the term of this patent is extended or adjusted under 35 U.S.C. 154(b) by 71 days.

(21) Appl. No.: 18/806,233

(22) Filed: Aug. 15, 2024

Related U.S. Application Data

(60) Provisional application No. 63/520,301, filed on Aug. 17, 2023.

(51) Int. Cl.
*A61N 1/05* (2006.01)

(52) U.S. Cl.
CPC .................................. *A61N 1/0531* (2013.01)

(58) Field of Classification Search
CPC ... A61B 5/293; A61B 2562/046; A61B 5/262; A61B 17/3403; A61B 17/3468; A61B 2017/00526; A61B 2017/3405; A61B 2017/3409; A61B 2017/3411; A61B 2018/1425; A61B 2050/005; A61B 2090/036; A61B 2560/0418; A61B 2560/0425; A61B 2560/0468; A61B 2562/0209; A61B 2562/0233; A61B 2562/028; A61B 2562/12; A61B 2562/125; A61B 2562/16; A61B 34/30;
(Continued)

(56) References Cited

U.S. PATENT DOCUMENTS

| | | | |
|---|---|---|---|
| 3,982,529 | A | 9/1976 | Sato |
| 5,008,733 | A | 4/1991 | Mine et al. |

(Continued)

FOREIGN PATENT DOCUMENTS

| | | | |
|---|---|---|---|
| EP | 2495011 | A1 | 9/2012 |
| WO | WO-2011139777 | A2 | 11/2011 |

(Continued)

OTHER PUBLICATIONS

Angle et al. Neuronal Recordings with Solid-Conductor Intracellular Nanoelectrodes (SCINEs). PLOS One 7(8):E43194 (Aug. 2012). 8 pages.

(Continued)

*Primary Examiner* — Mohamed G Gabr
(74) *Attorney, Agent, or Firm* — Wilson Sonsini Goodrich & Rosati

(57) ABSTRACT

In some aspects, the present disclosure provides a device for inserting an implant into a tissue in the central nervous system of a subject. In some embodiments, the device includes an implant support in mechanical communication with an implant. In some embodiments, the device includes a propulsion mechanism configured to propel the implant towards the tissue at a first time. In some embodiments, the device includes a triggering mechanism configured to activate a retraction mechanism at a second time, wherein the retraction mechanism is configured to retract the implant support upon activation. In some embodiments, a duration of time elapsed between the first time and the second time is less than 200 milliseconds.

20 Claims, 16 Drawing Sheets

(58) Field of Classification Search

CPC ... A61B 5/0051; A61B 5/0053; A61B 5/0057; A61B 5/0084; A61B 5/065; A61B 5/1111; A61B 5/1473; A61B 5/24; A61B 5/25; A61B 5/251; A61B 5/276; A61B 5/287; A61B 5/291; A61B 5/294; A61B 5/4547; A61B 5/6843; A61B 5/6847; A61B 5/6848; A61B 5/6849; A61B 5/685; A61B 5/688; A61B 5/6882; A61B 5/742; A61B 5/743; A61B 5/746; A61B 50/00; A61B 9/00; A61B 90/06; A61B 90/11; A61N 1/0531; A61N 1/0534; A61N 1/05; A61N 1/0529; A61N 1/0536; A61N 1/0539; A61N 2005/063; A61N 2005/0651; A61N 5/0601; A61N 5/0622; A61N 5/067; A61C 17/224; A61C 19/04

See application file for complete search history.

(56) References Cited

U.S. PATENT DOCUMENTS 5,721,450 A 2/1998 Miles
5,814,122 A 9/1998 Huang
6,049,038 A 4/2000 Suzuki
6,156,978 A 12/2000 Peck et al.
6,249,965 B1 6/2001 Bullara et al.
6,393,327 B1 5/2002 Scribner
6,511,463 B1 1/2003 Wood et al.
6,647,297 B2 11/2003 Scribner et al.
6,815,258 B2 11/2004 Vincent
6,920,359 B2 7/2005 Meadows et al.
6,940,182 B2 9/2005 Hilton et al.
7,091,060 B2 8/2006 Bolken et al.
7,134,198 B2 11/2006 Nakatani et al.
7,306,976 B2 12/2007 Feustel et al.
7,991,475 B1 8/2011 Tang et al.
8,010,208 B2 8/2011 Nimer et al.
8,024,049 B1 9/2011 Gilson et al.
8,280,516 B2 10/2012 Graupe
8,406,889 B2 3/2013 Llinas et al.
8,412,332 B2 4/2013 Massoud-Ansari et al.
8,649,873 B2 2/2014 Moffitt et al.
8,798,737 B2 8/2014 Merz et al.
8,805,530 B2 8/2014 John
8,849,408 B1 9/2014 Gilson et al.
8,929,992 B2 1/2015 Toader et al.
8,944,985 B2 2/2015 Bonmassar et al.
8,991,680 B1 3/2015 Schulman et al.
10,327,655 B2 6/2019 Angle et al.
10,390,724 B2 8/2019 Fonash et al.
10,799,132 B2 10/2020 Negi et al.
11,395,924 B2 7/2022 McLaughlin et al.
11,401,620 B2 8/2022 Kong et al.
12,171,995 B1 12/2024 Reid et al.
2002/0014688 A1 2/2002 Ramalingam et al.
2003/0100823 A1 5/2003 Kipke et al.
2004/0006264 A1 1/2004 Mojarradi et al.
2004/0026792 A1 2/2004 Vincent
2004/0034368 A1 2/2004 Pless et al.
2004/0119169 A1 6/2004 Hanawa
2004/0133118 A1 7/2004 Llinas
2004/0222010 A1 11/2004 Tonucci et al.
2005/0217796 A1 10/2005 Carter et al.
2005/0267347 A1 12/2005 Oster
2006/0172179 A1 8/2006 Gu et al.
2006/0206161 A1 9/2006 Nicolelis et al.
2006/0265039 A1 11/2006 Bartic et al.
2007/0106143 A1 5/2007 Flaherty
2007/0142872 A1 6/2007 Mickle et al.
2007/0250142 A1 10/2007 Francis et al.
2008/0140159 A1 6/2008 Bornhoft et al.
2008/0170819 A1 7/2008 Kodama et al.
2008/0205829 A1 8/2008 Jacobsen et al.
2008/0208283 A1 8/2008 Vetter et al.
2009/0004471 A1 1/2009 Amthor
2009/0069706 A1 3/2009 Boogaard et al.
2009/0120216 A1 5/2009 Chiou et al.
2009/0304774 A1 12/2009 Liang et al.
2010/0016928 A1 1/2010 Zdeblick et al.
2010/0029148 A1 2/2010 Perlin et al.
2010/0069776 A1 3/2010 Greger et al.
2010/0114272 A1 5/2010 Haidarliu et al.
2010/0133697 A1 6/2010 Nilsson
2010/0161019 A1 6/2010 Clark et al.
2011/0208031 A1 8/2011 Wolfe et al.
2012/0041294 A1 2/2012 Bai
2012/0109262 A1 5/2012 Martens et al.
2012/0279852 A1 11/2012 Zach
2013/0030500 A1 1/2013 Toader et al.
2013/0175733 A1 7/2013 De et al.
2013/0190586 A1 7/2013 Akingba et al.
2013/0190851 A1 7/2013 Schouenborg et al.
2013/0204317 A1 8/2013 Sauter-Starace et al.
2013/0274843 A1 10/2013 Barker et al.
2013/0337583 A1 12/2013 Kobayashi et al.
2014/0094674 A1 4/2014 Nurmikko et al.
2014/0107728 A1 4/2014 Fried et al.
2014/0309548 A1 10/2014 Merz et al.
2014/0330354 A1 11/2014 Shelton et al.
2014/0350634 A1 11/2014 Grill et al.
2015/0005573 A1 1/2015 Lehmann et al.
2015/0065831 A1 3/2015 Popovic et al.
2015/0224299 A1 8/2015 Wahlstrand
2015/0368822 A1 12/2015 Sammelselg et al.
2016/0029998 A1 2/2016 Brister et al.
2016/0049293 A1 2/2016 Li et al.
2016/0074655 A1 3/2016 Mercanzini et al.
2016/0128588 A1 5/2016 Melosh et al.
2016/0235967 A1 8/2016 Shan et al.
2016/0302687 A1 10/2016 Lee et al.
2017/0007813 A1 1/2017 Negi et al.
2017/0157407 A1 6/2017 Zellmer et al.
2017/0271919 A1 9/2017 Von Novak, III et al.
2017/0290521 A1 10/2017 Angle et al.
2017/0358488 A1 12/2017 Cho et al.
2018/0160929 A1 6/2018 Ashe et al.
2018/0221663 A1 8/2018 Saini
2018/0345019 A1 12/2018 Greenberg et al.
2019/0076644 A1 3/2019 Olson
2019/0175902 A1 6/2019 Lee et al.
2019/0388678 A1 12/2019 Najafi et al.
2020/0206516 A1 7/2020 Zellmer et al.
2020/0215335 A1 7/2020 McLaughlin et al.
2020/0315477 A1 10/2020 Constandinou et al.
2021/0098341 A1 4/2021 Kong et al.
2021/0138249 A1 5/2021 Howard
2021/0310988 A1 10/2021 McGrath et al.
2022/0175320 A1 6/2022 Shah et al.
2023/0225728 A1* 7/2023 List .................... A61B 5/14503 227/175.1

FOREIGN PATENT DOCUMENTS

WO WO-2017127551 A1 7/2017
WO WO-2017180482 A1 10/2017
WO WO-2018055369 A1 3/2018
WO WO-2018183967 A1 10/2018
WO WO-2024086542 A1 4/2024

OTHER PUBLICATIONS

Applied Materials Brochure. Enabling Next Generation Electronic Medical Devices With Atomic Layer Deposition. 1-9. No date or author available.

Astaneh, et al. Atomic Layer Deposition on Dental Materials: Processing Conditions and Surface Functionalization to Improve Physical, Chemical, and Clinical Properties—A Review. Acta Biomaterialia 121:103-118 (2021).

Bashkatov et al. Optical Properties of the Subcutaneous Adipose Tissue in the Spectral Range 400-2500 nm. Optics and Spectroscopy, vol. 99, No. 5, 2005, pp. 836-842.

(56) References Cited

OTHER PUBLICATIONS

Blomberg, et al. Atomic Layer Deposition Coatings for Medical Devices. ECS Meeting Abstracts, vol. MA2019-02, G02-Atomic Layer Deposition Applications 15:1126, 1-4 (2019). (Abstract Only).
Bouton, C. et al., Restoring cortical control of functional movement in a human with quadriplegia. Nature (2016). 13 pages. Retrieved Feb. 15, 2023 at URL: https://www.researchgate.net/profile/Marcia-Bockbrader/publication/301247939_Restoring_cortical_control_of_functional_movement_in_a_human_with_quadriplegia/links/59d70c77a6fdcc52acaa0075/Restoring-cortical-control-of functional-movement-in-a-human-with-quadriplegia.pdf.
Brenner, W. Use underfill encapsulants to enhance flip-chip assembly reliability. Electronic Design. Jul. 30, 2012; Retrieved Feb. 29, 2016 available at http://electronicdesign.com/boards/useunderfillencapsulantsenhanceflipchipassemblyreliability.
Co-pending U.S. Appl. No. 17/856,843, inventors Angle; Matthew et al., filed Jul. 1, 2022.
Co-pending U.S. Appl. No. 18/053,106, inventors Angle; Matthew et al., filed Nov. 7, 2022.
Co-pending U.S. Appl. No. 18/177,024, inventors Landry; Michael et al., filed Mar. 1, 2023.
Co-pending U.S. Appl. No. 18/184,572, inventors Burrows; James et al., filed Mar. 15, 2023.
Co-pending U.S. Appl. No. 18/316,127, inventor Burrows; James, filed May 11, 2023.
Co-pending U.S. Appl. No. 18/329,485, inventors Angle; Matthew et al., filed Jun. 5, 2023.
Co-pending U.S. Appl. No. 18/342,602, inventors Angle; Matthew et al., filed Jun. 27, 2023.
Co-pending U.S. Appl. No. 18/934,011, inventors Angle; Matthew et al., filed Oct. 31, 2024.
Ghelich, et al. Unprotected Sidewalls of Implantable Silicon-based Neural Probes and Conformal Coating as a Solution. Npj Materials Degradation 5:1-16 (2021).
Goto, Kazuya et al. Transcutaneous photocoupler for transmission of biological signals. Optics Letters 27(20):1797-1799 (2002).
Hajjhassan et al. NeuroMEMS: Neural Probe Microtechnologies. Sensors 8(10):6704-6726 (Oct. 25, 2008). doi: https://doi.org/10.3390/s8106704.
Instruction for use (IFU) Blackrock research assemblies. Blackrock Microsystems, LLC. 2014. pp. 0-13.
International Search Report dated Jun. 19, 2017 for International Application No. PCT/US2017/026707.
Johnson, L.J. et al., A novel high electrode count spike recording array using an 81,920 pixel transimpedance amplifier-based imaging chip. Journal of Neuroscience methods. 205; 2012: 223-232.
Johnson, R. Wayne, Chapter 19: Flip Chip Assembly and underfilling, Auburn University (2001). Available at https://pdfs.semanticscholar.org/3c24/524ef9ede82c95ba10caae142e3ca8b58966.pdf.
Li, et al. Ultra-Long-Term Reliable Encapsulation Using an Atomic Layer Deposited HfO2/Al2O3/HfO2 Triple-Interlayer for Biomedical Implants. Coatings 9:579, 1-13 (2019).
Liao et al. Fabrication of high aspect ratio microstructure arrays by micro reverse wire-EDM. J. Micromech. Microeng. 15 (2005) 1547-1555.
Mauron, F. Improvements in glass encapsulation technology offer significant advantages for implantable medical devices. Valtronic. p. 1-10. Jul. 2013. Retrieved Mar. 2, 2023 at URL: http://www.implantable-device.com/wp-content/uploads/2013/07/Valtronic-Glass-Encapsulation-White-Paper.pdf.
Office Action dated Jun. 30, 2017 for U.S. Appl. No. 15/482,583.
Office Action dated Nov. 28, 2017 for U.S. Appl. No. 15/482,583.
PCT/US2018/025576 International Search Report and Written Opinion dated Jul. 30, 2018.
PCT/US2023/077021 International Search Report and Written Opinion dated Feb. 22, 2024.
Scribner, D. et al., A retinal prosthesis technology based on CMOS microelectronics and microwire glass electrodes. IEEE transactions on biomedical circuits and systems, 1(1); Mar. 2007: p. 73-84.
Stolp et al. Immune responses at brain barriers and implications for brain development and neurological function in later life. Frontiers in Integrative Neuroscience, vol. 7, Article 61 (Aug. 23, 2013). 14 pages.
U.S. Appl. No. 15/482,583 Notice of Allowance dated Mar. 6, 2019.
U.S. Appl. No. 16/584,630 Notice of Allowance dated Apr. 27, 2022.
U.S. Appl. No. 16/584,630 Notice of Allowance dated May 26, 2022.
U.S. Appl. No. 15/482,583 Office Action dated Aug. 28, 2018.
U.S. Appl. No. 15/482,583 Notice of Allowance dated Apr. 23, 2019.
U.S. Appl. No. 15/482,583 Notice of Allowance dated Mar. 20, 2019.
U.S. Appl. No. 16/584,630 Office Action dated Mar. 1, 2022.
U.S. Appl. No. 17/031,584 Office Action dated Apr. 18, 2023.
U.S. Appl. No. 17/031,584 Office Action dated Dec. 15, 2023.
U.S. Appl. No. 17/031,584 Office Action dated Feb. 11, 2025.
U.S. Appl. No. 17/031,584 Office Action dated May 17, 2024.
U.S. Appl. No. 17/937,374 Notice of Allowance dated Nov. 5, 2024.
U.S. Appl. No. 17/937,374 Notice of Allowance dated Sep. 18, 2024.
U.S. Appl. No. 17/937,374 Office Action dated Jun. 12, 2024.
U.S. Appl. No. 17/937,374 Supplemental Notice of Allowability dated Nov. 18, 2024.
Webb, James Luke. et al. Detection of biological signals from a live mammalian muscle using an early stage diamond quantum sensor. Scientific Reports 11:2412, 1-11 (2021).
U.S. Appl. No. 17/031,584 Office Action dated Apr. 30, 2026.
U.S. Appl. No. 17/856,843 Office Action dated Feb. 24, 2026.
U.S. Appl. No. 18/053,106 Office Action dated Mar. 3, 2026.
U.S. Appl. No. 18/177,024 Notice of Allowance dated Apr. 29, 2026.
U.S. Appl. No. 18/316,127 Office Action dated Mar. 4, 2026.
U.S. Appl. No. 18/342,602 Office Action dated Feb. 24, 2026.

* cited by examiner

SYSTEMS, DEVICES, AND METHODS FOR INSERTING ARRAYS

CROSS-REFERENCE

This application claims the benefit of U.S. Provisional Application No. 63/520,301, filed Aug. 17, 2023, which application is incorporated herein by reference.

STATEMENT AS TO FEDERALLY SPONSORED RESEARCH

This invention was made with United States Government support under Contract No. NIH R44MH125700 funded by The National Institutes of Health. The Government has certain rights in this invention.

BACKGROUND

Medical devices such as implants are used for a wide array of purposes. Implanting these implants into tissue can often be imprecise, difficult, and arduous, particularly when the tissue is an internal tissue. Devices and methods used to help with implantation are often times difficult to maneuver, prone to error, or cannot easily maintain sterility of the implant. There is a need for a device for implantation of implants that is precise, performs implantation quickly, and maintains sterility of the implant and related devices.

SUMMARY

In some aspects, the present disclosure provides a device for inserting an implant into a tissue in the central nervous system of a subject, comprising: an implant support in mechanical communication with an implant; a propulsion mechanism configured to propel the implant towards the tissue at a first time; and a triggering mechanism configured to activate a retraction mechanism at a second time, wherein the retraction mechanism is configured to retract the implant support upon activation, wherein a duration of time elapsed between the first time and the second time is less than 200 milliseconds.

In some aspects, the present disclosure provides a device for inserting an implant into a tissue in the central nervous system of a subject, comprising a propulsion mechanism configured to propel the implant towards the tissue, wherein the propulsion mechanism comprises an internal energy source configured to propel the implant towards the tissue with a velocity sufficient to insert the implant into the tissue to a predetermined depth, wherein the internal energy source is within a sterile field of the device.

In some aspects, the present disclosure provides a device for inserting an implant into a tissue in the central nervous system of a subject, comprising a propulsion mechanism configured to propel the implant towards the tissue, wherein the propulsion mechanism does not require an external energy source to propel the implant towards the tissue with a velocity sufficient to insert the implant into the tissue to a predetermined depth, wherein the external energy source is external to a sterile field of the device.

In some aspects, the present disclosure provides a device for inserting an implant into a tissue in the central nervous system of a subject, comprising a propulsion mechanism configured to propel the implant towards the tissue, wherein at least 20% of a kinetic energy of the implant, when propelled, is generated from an energy source within a housing of the device.

In some aspects, the present disclosure provides a device for inserting an implant into a tissue in the central nervous system of a subject, comprising a propulsion mechanism configured to propel the implant towards the tissue, wherein less than 20% of a kinetic energy of the implant, when propelled, is generated from a compressor.

In some embodiments, the propulsion mechanism comprises an internal energy source configured to propel the implant towards the tissue with a velocity sufficient to insert the implant into the tissue to a predetermined depth, wherein the internal energy source is within a sterile field of the device.

In some embodiments, the propulsion mechanism does not require an external energy source to propel the implant towards the tissue with a velocity sufficient to insert the implant into the tissue to a predetermined depth, wherein the external energy source is external to a sterile field of the device.

In some embodiments, at least 20% of a kinetic energy of the implant, when propelled, is provided from an energy source within a housing of the device.

In some embodiments, less than 20% of a kinetic energy of the implant, when propelled, is provided from an external positive pressure source.

In some embodiments, the external positive pressure source comprises a pneumatic positive pressure source.

In some embodiments, the pneumatic positive pressure source comprises a compressor.

In some embodiments, the device further comprises an implant support in mechanical communication with the implant, and further comprises a retraction mechanism configured to retract the implant support when the retraction mechanism is activated.

In some embodiments, the retraction mechanism is configured to begin retraction the implant support after the propulsion mechanism propels the implant towards the tissue at the first time.

In some embodiments, the retraction mechanism is configured to begin retraction of the implant support before the propulsion mechanism propels the implant towards the tissue at the first time.

In some embodiments, the retraction mechanism is configured to retract the implant support before the implant is inserted in the tissue of the central nervous system.

In some embodiments, the retraction mechanism is configured to retract the implant support less than 10, 9, 8, 7, 6, 5, 4, 3, 2, or 1 milliseconds before the implant is inserted in the tissue of the central nervous system.

In some embodiments, the retraction mechanism is configured to retract the implant support when the implant is less than 5, 4, 3, 2, 1, 0.5, or 0.1 mm from the tissue.

In some embodiments, the duration of time elapsed between the first time and the second time is less than 100 milliseconds.

In some embodiments, the duration of time elapsed between the first time and the second time is less than 90, 80, 70, 60, 50, 40, 30, 20, 10, 9, 8, 7, 6, 5, 4, 3, 2, 1, 0.5, 0.1, 0.05, or 0.01 milliseconds.

In some embodiments, the triggering mechanism comprises ball bearings.

In some embodiments, the triggering mechanism actuates via a change in the position of ball bearings within the device.

In some embodiments, the implant is propelled towards the tissue at an initial velocity of about 1 to 20 meters/second (m/s).

In some embodiments, the initial velocity is about 2 to 8 m/s.

In some embodiments, the device is configured to avoid contacting the tissue or the implant after the implant is inserted into the tissue.

In some embodiments, the device further comprises a firing mechanism configured to activate the propulsion mechanism.

In some embodiments, the firing mechanism comprises a firing turn key.

In some embodiments, activating the firing mechanism comprises turning the firing turn key.

In some embodiments, the firing mechanism comprises a manually activated mechanism.

In some embodiments, the firing mechanism comprises an electronically activated mechanism.

In some embodiments, the firing mechanism is configured to prevent rotation of the propulsion mechanism upon firing.

In some embodiments, the firing mechanism comprises a pin to prevent rotation of the propulsion mechanism.

In some embodiments, the implant support comprises a gripping mechanism.

In some embodiments, the gripping mechanism comprises a collet.

In some embodiments, the collet grips the implant when in a first state.

In some embodiments, flexure prongs of the collet grip the implant when the device is in the first state.

In some embodiments, the collet is protracted from a distal end of the device when in the first state.

In some embodiments, the collet does not grip the implant when in a second state.

In some embodiments, flexure prongs of the collet do not grip the implant when the device is in the second state.

In some embodiments, the collet is retracted into the device when in the second state.

In some embodiments, the propulsion mechanism contacts flexure prongs of the collet after firing, thereby opening the flexure prongs and releasing the implant.

In some embodiments, the implant support is configured to protect the implant from mechanical damage until the implant is inserted.

In some embodiments, the implant comprises a plurality of electrodes.

In some embodiments, the plurality of electrodes comprises a plurality of contact regions.

In some embodiments, the plurality of electrodes each comprises a contact region in the plurality of electrode contacts.

In some embodiments, the plurality of contact regions comprises at least 2, 5, 10, 20, 50, 100, 500, or 1000 contacts.

In some embodiments, the plurality of electrode contact regions comprise a density of 1 to 25, 2 to 20, or 4 to 16 contacts per square millimeter.

In some aspects, the present disclosure provides a kit comprising a hermetically sealed package, wherein the hermetically sealed package comprises a device configured to insert an implant into a tissue in the central nervous system of a subject upon activation.

In some aspects, the present disclosure provides a kit comprising: a first package, comprising a device configured to insert the implant into a tissue in the central nervous system of a subject upon activation; a hermetically sealed package, comprising an implant; and wherein the device and the implant are configured to be assembled.

In some embodiments, the hermetically sealed package further comprises the implant.

In some embodiments, the implant and the device are coupled.

In some embodiments, the first package is hermetically sealed.

In some embodiments, the implant is sterilized.

In some embodiments, the device is sterilized.

In some embodiments, the kit comprises instructions for using the device.

In some embodiments, the kit comprises a code for associating the implant with a subject recipient of the implant.

In some aspects, the present disclosure provides a method for inserting an implant into a tissue in the central nervous system of a subject, comprising: providing a device configured to propel the implant from the device, wherein the device is configured to activate a retraction mechanism when the implant is propelled from 35% to 75% of a total travel distance to a target area; aiming the device at the target area of the tissue of the subject; and firing the device to propel the implant to the target area, thereby inserting the implant in the tissue of the subject at the total travel distance.

In some aspects, the present disclosure provides a method for inserting an implant into a tissue in the central nervous system of a subject, comprising: providing a device configured to propel the implant from the device; aiming, at an angle of at least 30 degrees from the direction of gravity, the device at the target area of the tissue of the subject; and firing the device to propel the implant to the target area, thereby inserting the implant in the tissue of the subject.

In some aspects, the present disclosure provides a method of inserting an implant into a tissue in the central nervous system of a subject comprising: providing a device configured to propel the implant from the device, wherein the implant is mechanically coupled to the device; placing a distal end of the device next to the tissue of the subject; and firing the device to propel the implant to the target area, thereby inserting the implant in the tissue of the subject.

In some embodiments, the distal end of the device contacts the tissue of the subject.

In some embodiments, there is an air gap between the implant and the tissue before firing the device.

In some embodiments, the device is configured to activate a retraction mechanism when the implant is propelled from 35% to 75% of a total travel distance to a target area.

In some embodiments, the aiming comprises aiming, at an angle of at least 30 degrees from the direction of gravity, the device at the target area of the tissue of the subject.

In some embodiments, the total travel distance is from 2 mm to 4 mm, or about 2.9 mm.

In some embodiments, at least a portion of the implant is inserted from 0.5 mm to 3.0 mm into the tissue.

In some embodiments, the tissue comprises a neural tissue.

In some embodiments, the neural tissue comprises neural cells.

In some embodiments, the neural tissue comprises glial cells.

In some embodiments, the tissue comprises epithelial tissue, connective tissue, vascular tissue, or any combination thereof.

In some embodiments, the tissue comprises a meninx, a blood vessel, a blood-brain barrier tissue, or any combination thereof.

In some embodiments, the meninx comprises a pia mater, a dura mater, an arachnoid mater, or any combination thereof.

In some embodiments, the neural tissue comprises a brain tissue.

In some embodiments, the brain tissue comprises a cortical brain tissue.

In some embodiments, the cortical brain tissue comprises a tissue in the primary motor cortex.

In some embodiments, the cortical brain tissue comprises a tissue in the secondary motor cortex.

In some embodiments, the cortical brain tissue comprises a tissue in the premotor cortex.

In some embodiments, the tissue forms at least a part of a spinal cord, a peripheral nerve, an auditory cortical area, or a somatosensory cortical area.

In some embodiments, the subject is a mammal.

In some embodiments, the subject is a bovine, an ungulate, a rodent, a canine, a feline, or a primate.

In some embodiments, the primate is a macaque.

In some embodiments, the primate is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
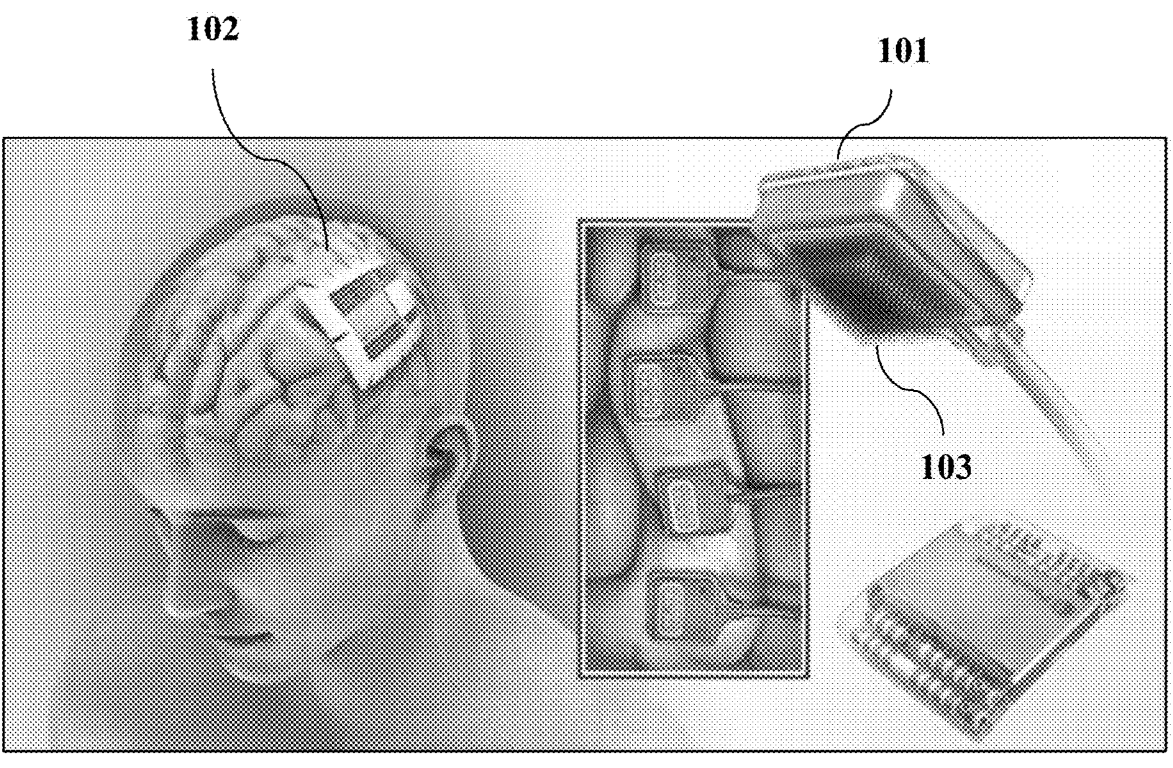
FIG. 1 provides an illustration of a subject who has multiple implants 101 inserted into a cortical region 102 of the subject's brain.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount, in some cases near the stated amount by 10%, 5%, or 1%, including increments therein, and in some cases, in reference to a percentage, refers to an amount that is greater or less the stated percentage by 10%, 5%, or 1%, including increments therein.

As used herein, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C", "one or more of A, B, or C" and "A, B, and/or C" means A alone, B alone, C alone, A and B together, A and C together, B and C together, or A, B and C together.

Reference throughout this specification to "some embodiments," "further embodiments," or "a particular embodiment," means that a particular feature, structure, or characteristic described in connection with the embodiment is included in at least one embodiment. Thus, the appearances of the phrase "in some embodiments," or "in further embodiments," or "in a particular embodiment" in various places throughout this specification are not necessarily all referring to the same embodiment. Furthermore, the particular features, structures, or characteristics may be combined in any suitable manner in one or more embodiments.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately after an initial event or within a short enough time span after such initial event, such as within at most 1 second, 0.5 seconds, 0.1 seconds, 0.05 seconds, 0.01 seconds, 5 milliseconds, 1 ms, 0.5 ms, 0.1 ms, 0.05 ms, 0.01 ms, 0.005 ms, 0.001 ms, 0.0005 ms, 0.0001 ms, or less.

Brain-computer interfaces (BCI) can be used to form a direct communication pathway between the brain's electrical activity and a digital computer. BCIs are often directed at researching, mapping, assisting, augmenting, or repairing human cognitive or sensory-motor functions. More specifically, BCIs can be used to study basic neural mechanisms behind cortical function and disease. They can be used in clinical research in restoring lost functions, e.g., paralysis. The development of brain-computer interfaces that can measure and record electrical activity from many thousands of neurons while minimizing damage to healthy brain tissue is an ongoing field of research. Advances in BCIs trend towards fully-implantable devices designed for long-term daily service with increases in the number of individual neural signals for input and output.

Increasing the number of individual neural signals can unlock new and more complex capabilities for BCIs. Increasing the number of signals can be achieved by: (1) increasing the density of electrodes provided in an implant, and (2) increasing the number of implants. FIG. 1 provides an illustration of a subject who has multiple implants 101 inserted into a cortical region 102 of the subject's brain. The implant comprises a highly dense array of electrodes 103, which can each be configured to receive or output individual electrical signals. The electrode array can comprise, for example, a density of 16 electrodes per square millimeter with each electrode having an electrical contact region at the tip. The electrode array can comprise, for example, a density of more than 16 electrodes per square millimeter with each electrode having an electrical contact region at the tip. Multiple of these implants can be inserted in various areas of the brain to increase the amount of neural activity data received by the electrodes. However, these advances pose new challenges for surgical methods and tools.

The insertion of the microelectrode arrays into the brains of humans and other mammals can result in deformation of the underlying brain tissue and trauma to the brain. The brain tissue can deform significantly prior to and during being penetrated by a microelectrode, which can cause tissue damage and loss of neurons. This 'dimpling problem' can be even more pronounced for implants with many electrodes, especially if the electrodes are closely spaced.

Figure 2:
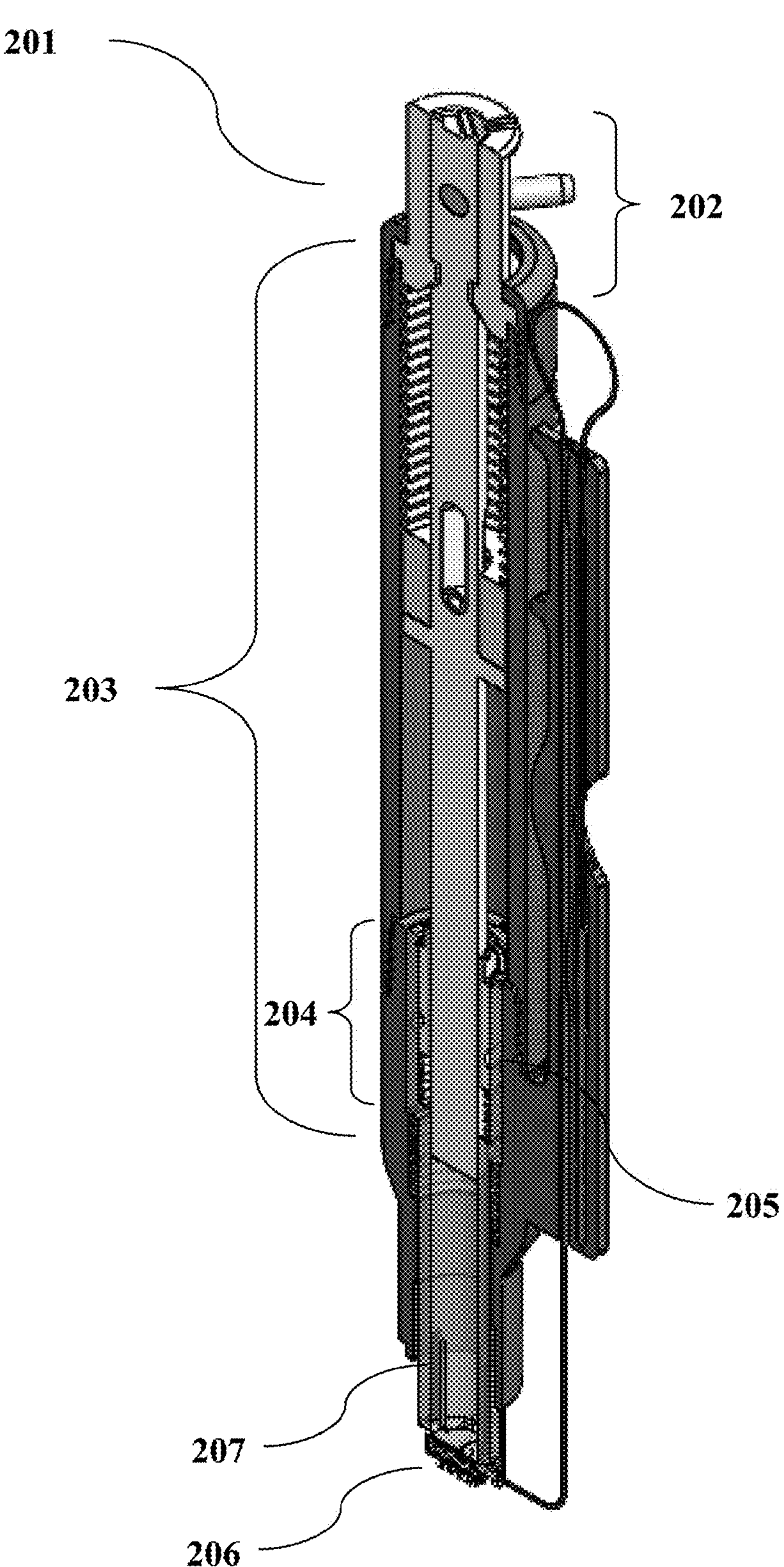
FIG. 2 shows a cross-sectional view of an embodiment of a device 201, which comprises a firing mechanism 202, a propulsion mechanism 203, a retraction mechanism 204, and a triggering mechanism 205.

To overcome the dimpling problem, one procedure for inserting the electrode into tissue is to propel the implant into the tissue at a high velocity. When the velocity is sufficiently high, the numerous electrode contacts of the implant can penetrate the tissue at once. To perform this procedure safely, the present disclosure provides a device for propelling the implant into the tissue while substantially preventing or minimizing the risk of a "double tap". A "double tap" can refer to a secondary contact made by the device with the subject (the primary contact being the first contact made when the implant is inserted into the target tissue), which can deliver mechanical damage to the target tissue or a proximal region thereof. As the kinetic energy involved in accelerating the implant to high velocity can be very high, unmitigated "double tapping" can deliver high amounts of mechanical energy to the subject, injuring the subject. In some aspects, the present disclosure provides devices comprising various mechanisms which are configured to propel the implant while preventing secondary contact. FIG. 2 shows a cross-sectional view of an embodiment of such a device 201, which comprises a firing mechanism 202, a propulsion mechanism 203, a retraction mechanism 204, and a triggering mechanism 205. Various embodiments of the devices and its mechanisms are described with additional detail in the following sections.

Figure 3:
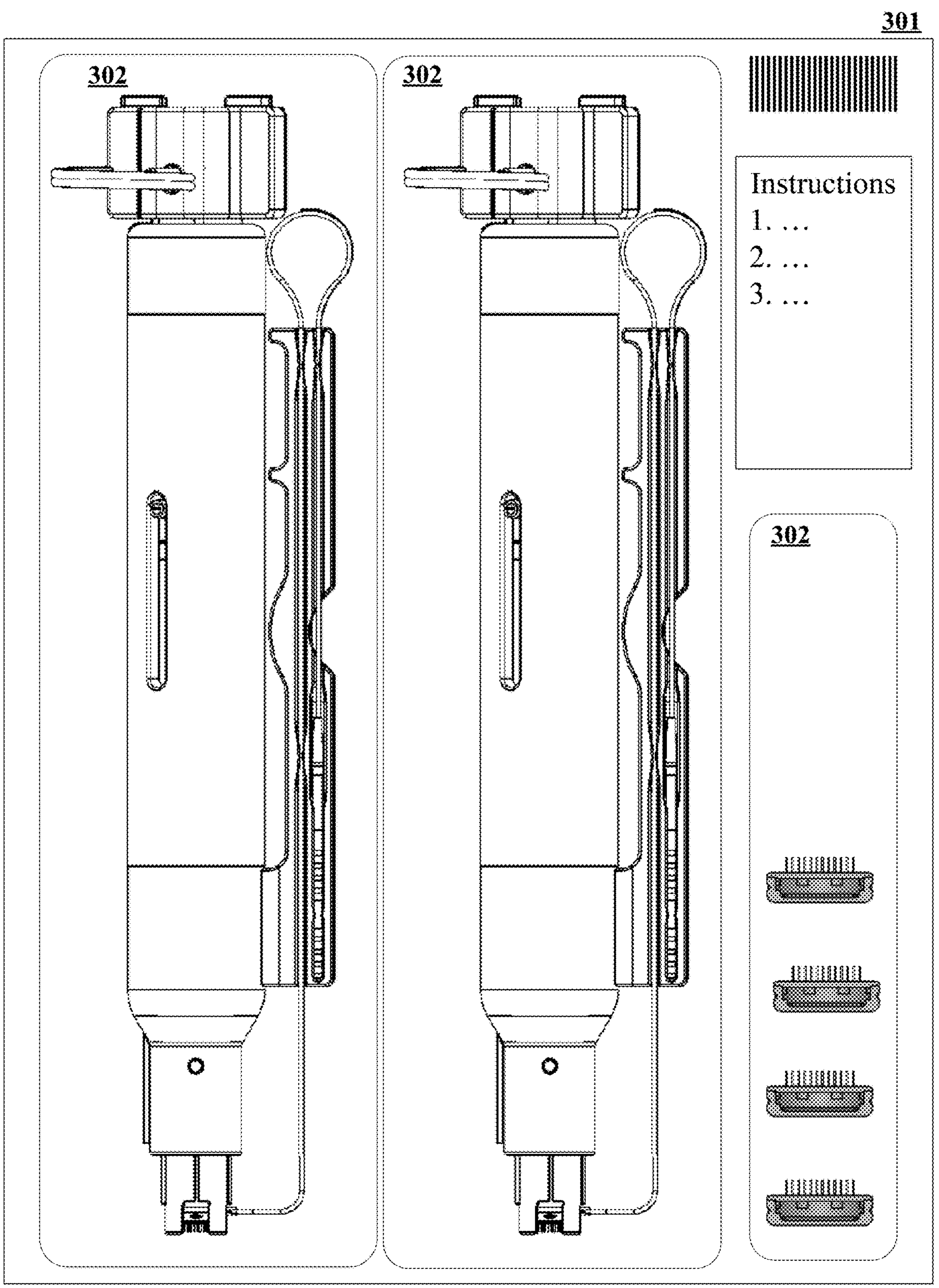
FIG. 3 shows an embodiment of a kit 301 comprising a device.

Inserting multiple implants also presents surgical challenges. Due to the blood-brain barrier, it may be challenging to prevent or manage infection risks after post-operation. Thus, it is highly desirable for the implant to be able to be inserted into the brain while making minimal contact with any surfaces (e.g., operating tables, surgeon's gloves, etc.) that may carry pathogens. In some aspects, devices of the present disclosure may be delivered in a "ready-to-fire" configuration in a sterilized package. FIG. 3 shows an embodiment of a kit 301 comprising a device. A kit can comprise any number of devices and any number of implants provided in one or more sterilized packages 302. Some devices may be provided already assembled with an implant, so that they can be used without requiring the assembly of the implant and the device before firing. Accordingly, a device can be used "out-of-the-box" in a "ready-to-fire" mode in the operating room. Various embodiments of the kits and its contents are described with additional detail in the following sections.

Figure 4:
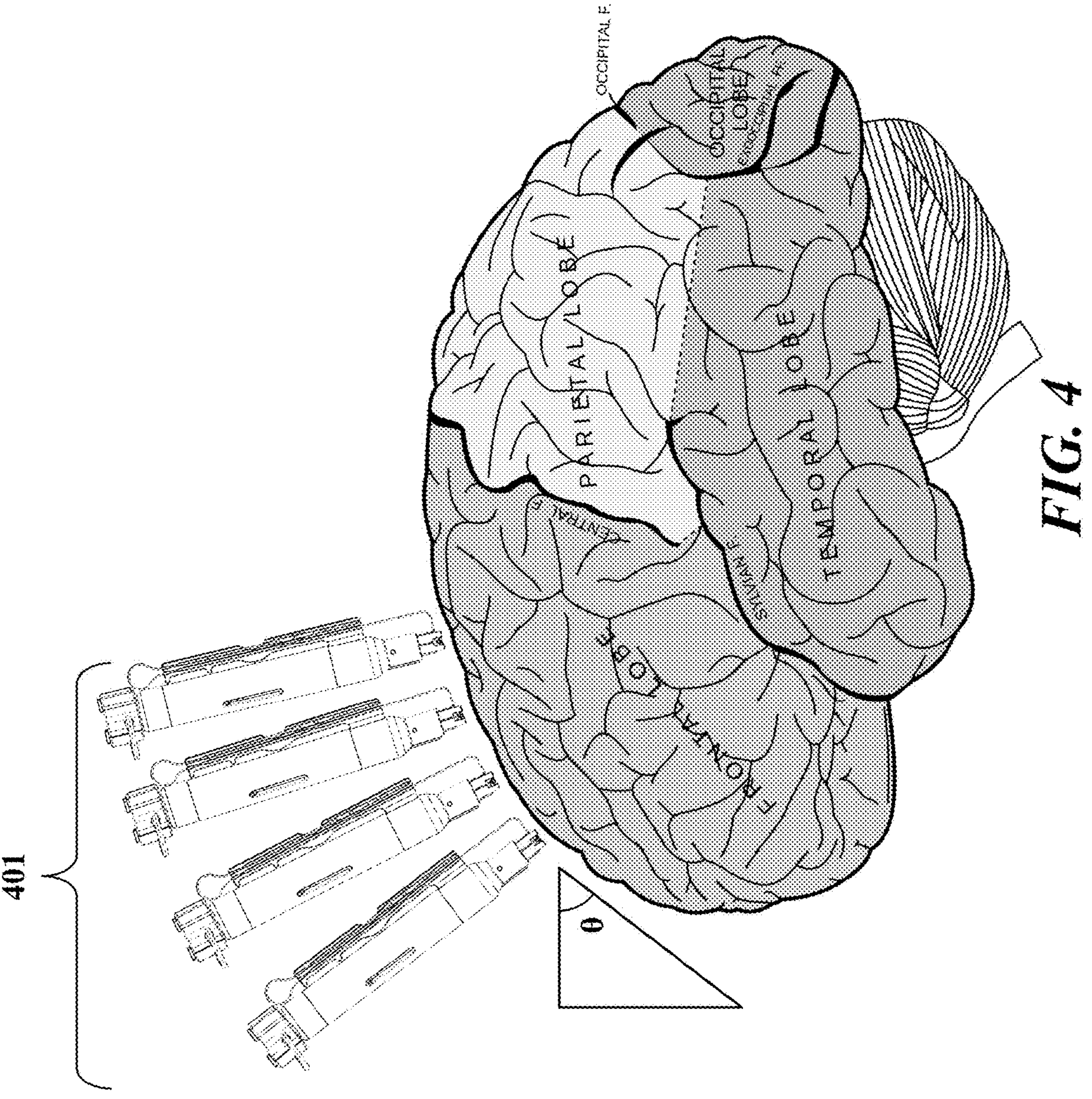
FIG. 4 shows an illustration of a procedure for inserting multiple implants into a brain.

The device, the implant, or both, can be provided in a sterilized kit such that multiple devices can be used in a sequence to insert multiple implants in quick succession. FIG. 4 shows an illustration of a procedure for inserting multiple implants into a brain. Because multiple devices 401 may come with their own energy source, they may be fired in quick succession without assembling the devices with an external energy source (e.g., a separate compressor).

Furthermore, the devices can be fired from multiple angles, θ, because the implant and the device can be provided already coupled with one another (e.g., even upside down). Accordingly, complex surgical operations can be performed quicker and more simply, even when implants need to be inserted from difficult angles. Various methods of using the devices disclosed herein are described with additional detail in the following sections.

Device

In some aspects, the present disclosure provides a device for inserting an implant into a tissue of a central nervous system of a subject. FIG. 2 shows a cross-sectional view of an embodiment of a device. The device 201 can comprise a firing mechanism 202 configured to activate a propulsion mechanism 203. The propulsion mechanism 203, when activated, can propel the implant 206 towards the tissue at a first time, e.g., a time at which a member of the propulsion mechanism contacts the implant. The implant may be coupled to the device by an implant support 207, which the propulsion mechanism may push upon. The device can comprise a triggering mechanism 205 configured to activate a retraction mechanism at a second time, e.g., within a time window relative to the first time. The retraction mechanism 204 can, when activated, retract the implant support, which can prevent or reduce the risk of a secondary contact occurring between the device and the inserted implant.

Firing Mechanism

The device can comprise a firing mechanism. The firing mechanism can be configured to activate the propulsion mechanism. The firing mechanism can be a separate piece from any other mechanism, or it can form a unitary piece with another mechanism. For example, the firing mechanism can be a separate piece from the propulsion mechanism, the retraction mechanism, the triggering mechanism, the implant support, or any combination thereof. The firing mechanism can be a unitary piece with the propulsion mechanism, the retraction mechanism, the triggering mechanism, the implant support, or any combination thereof.

The firing mechanism can be manually activated, or it can be electronically activated. For example, the firing mechanism can be activated solely through moving mechanical parts, without involvement of any electronics. The firing mechanism can be activated solely through electronic components, without involvement moving mechanical parts. In some embodiments, the firing mechanism can be activated using a combination of moving mechanical parts and electronic components. In some embodiments, the firing mechanism can be activated using pneumatic components.

The firing mechanism can be fired using a key or a button. The key or button can be turned, pulled, pushed, twisted, or used with other motion, to fire the device. In one example, the firing mechanism comprises a firing turn key 503. A firing turn key can be turned, which fires the propulsion mechanism. In another example, the firing mechanism can be fired using a button. The button can be, e.g., in wired or wireless communication with the device so that pressing the button activates the propulsion mechanism. The button can be disposed on the device, or it can be provided separately. Pressing the button can fire the firing mechanism.

The firing mechanism can be configured to prevent or reduce rotation of the propulsion mechanism, the implant support, or the implant before, during, or after firing. The firing mechanism can, e.g., comprise a pin 703 that fixes the propulsion mechanism, the implant support, or the implant at specified orientation with respect to the body of the device. Preventing or reducing rotation of the device components can reduce variation in the firing characteristics of the device. For example, a device during transport may be handled roughly (e.g., thrown, shaken, tumbled, etc.) which may increase the risk of the device mechanisms becoming misaligned. Providing a fixture that can fix the propulsion mechanism, the implant support, or the implant at specified orientation with respect to the body of the device, can reduce undesirable misalignment of any one of those components during transport.

Propulsion Mechanism

The device can comprise a propulsion mechanism. The propulsion mechanism can comprise an internal energy source configured to propel the implant towards the tissue. The internal energy source can be within a sterile field of the device. The internal energy source can be configured to propel the implant towards the tissue with a velocity sufficient to insert the implant into the tissue to a predetermined depth. In some embodiments, the propulsion mechanism does not require an external energy source to propel the implant towards the tissue with a velocity sufficient to insert the implant into the tissue to a predetermined depth.

In some embodiments, the propulsion mechanism can comprise a hammer 706. In some embodiments, the propulsion mechanism can comprise a spring 701. In some embodiments, the propulsion mechanism can comprise a plurality of springs 701 and 702. The hammer can be spring-loaded. The firing mechanism can be configured to release the plurality of springs in the propulsion mechanisms. Releasing the springs in the propulsion mechanism can propel the hammer towards the implant. The hammer can contact the implant, propelling the implant towards the tissue.

The propulsion mechanism can be configured to propel the implant towards the tissue at a first time. In some embodiments, the first time can be when a member or property of the propulsion mechanism begins to propel the implant towards the tissue. The first time can be when a member of the propulsion mechanism first contacts the implant. In some embodiments, the first time is the time at which the hammer 706 first contacts the implant. In some embodiments, the first time can be when a force or pressure of the propulsions mechanism first begins to drive the implant towards the tissue.

The sterile field can refer to surfaces or volumes within the device which are not directly exposed to the outside. For example, surfaces and volumes of the device within the housing of the device may be considered to be within the sterile field of the device. Meanwhile, surfaces of the device that a surgeon may touch (e.g., outside surface of the housing) may be considered not to be within the sterile field of the device. An internal energy source can be advantageous in that it can greatly simplify using the device. For example, if a device requires an external energy source, e.g., an external compressor to provide the energy for propelling an implant, using the device may require providing the external compressor separately, and it may also require coupling of the device with the external compressor, which may add unnecessary complexity to a surgical procedure. Thus, the propulsion mechanism may not require an external energy source to propel the implant towards the tissue. The external energy source may refer to an energy source that is external to a sterile field of the device (e.g., an external compressor). However, the device does not preclude using an external energy source. Less than 20% of a kinetic energy of the implant, when propelled, may be generated from an external energy source. In some embodiments, less than 50, 40, 30, 20, 10, 5, 4, 3, 2, or 1% of the kinetic energy of the implant, when propelled, may be generated from an external energy source, e.g., an external positive pressure source. In some embodiments, more than 0, 1, 2, 3, 4, 5, 10, 20, 30, or 40% of the kinetic energy of the implant, when propelled, may be generated from an external energy source. In some embodiments, at least 20, 30, 40, 50, 60, 70, 80, 90, 95, 96, 97, 98, 99, or 100% of a kinetic energy of the implant, when propelled, can be generated from an internal energy source. In some embodiments, at most 30, 40, 50, 60, 70, 80, 90, 95, 96, 97, 98, 99, or 100% of a kinetic energy of the implant, when propelled, can be generated from an internal energy source.

An internal energy source can comprise various forms. The internal energy source can comprise stored mechanical energy, e.g., a spring or a pressurized canister. The internal energy source can comprise chemical energy, e.g., combustible fuel or a battery. The internal energy source can comprise electromagnetic energy, e.g., a configuration of permanent or electro-magnets. In some embodiments, an internal energy source does not comprise or require a compressor, an external energy source, an external compressor, a pneumatic compressor, or an external pneumatic compressor.

Triggering Mechanism

The device can comprise a triggering mechanism configured to retract an implant support upon activation. The triggering mechanism can be configured to activate the retraction mechanism at a second time. In some embodiments, the duration of time between the first time and the second time can be the time between when a member or property of the propulsion mechanism first contacts the implant and when the triggering mechanism activates the retraction mechanism. In some specific embodiments, the duration of time between the first time and the second time can be the time between when a hammer of the propulsion mechanism first contacts the implant and the time when the triggering mechanism activates the retraction mechanism to retract the implant support. In some embodiments, the first time can occur before the second time, e.g., the hammer can contact the implant before the triggering mechanism activates the retraction mechanism. In some embodiments, the second time can occur before the first time, e.g., the hammer can contact the implant after the triggering mechanism activates the retraction mechanism. In some embodiments, the first time and the second time can be simultaneous, e.g., the hammer can contact the implant at the same time the triggering mechanism activates the retraction mechanism.

The duration of time elapsed from the first time to the second time can be less than 400, 300, 200, 150, 100, 90, 80, 70, 60, 50, 40, 30, 20, 15, 10, 9, 8, 7, 6, 5, 4, 3, 2, 1, 0.5, 0.1, 0.05, or 0.01 ms milliseconds. The duration of time elapsed from the first time to the second time can be greater than 0.01, 0.05, 0.1, 0.5, 1, 2, 3, 4, 5, 6, 7, 8, 9, 10, 15, 20, 30, 40, 50, 60, 80, 100, 150, 200, 300, or 400 milliseconds. The duration of time elapsed from the first time to the second time can be greater than −20, −15, −10, −9, −8, −7, −6, −5, −4, −3, −2, or −1 ms.

Figure 9:
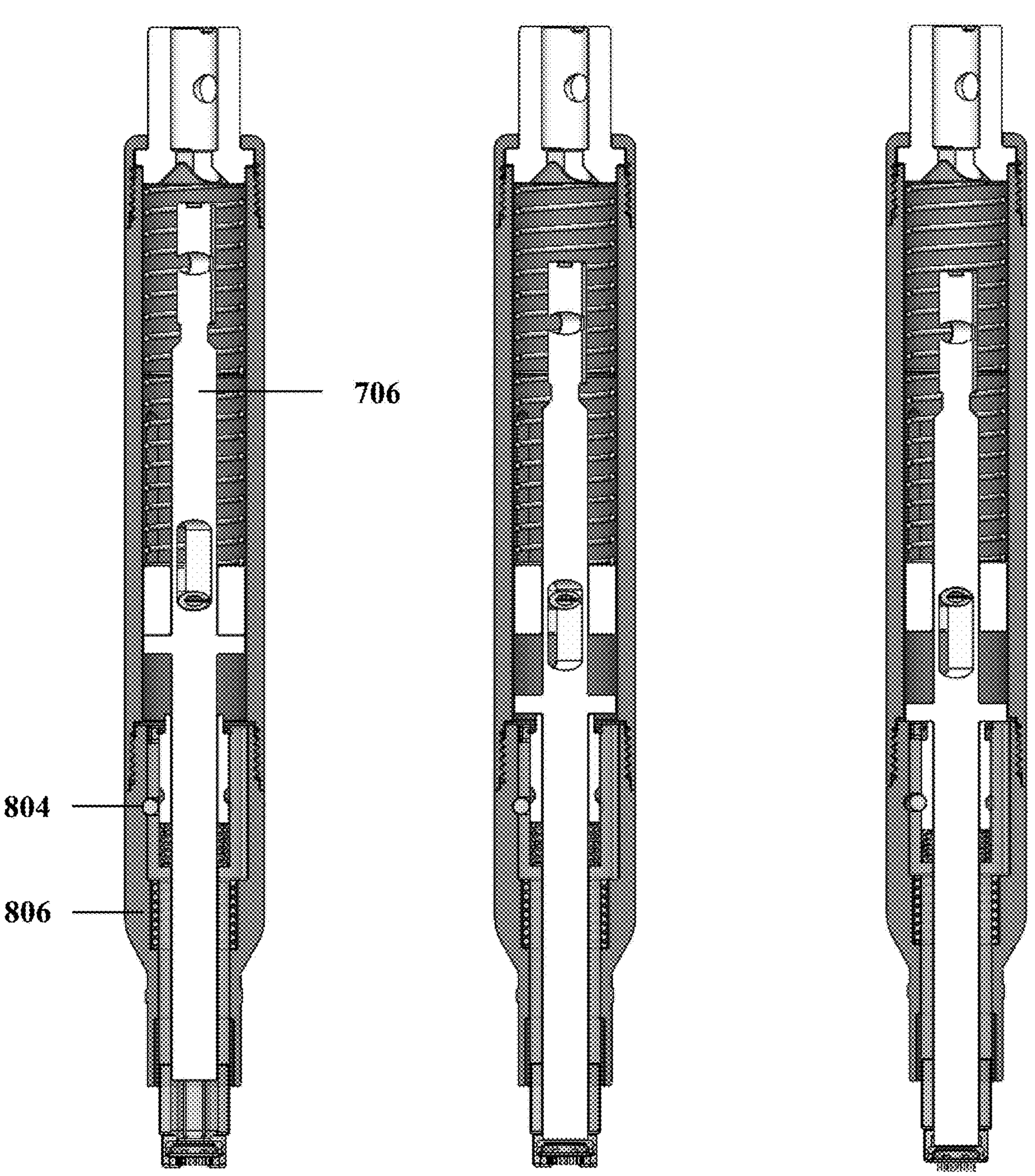
FIG. 9 illustrates motions of the triggering mechanism.
Figure 10:
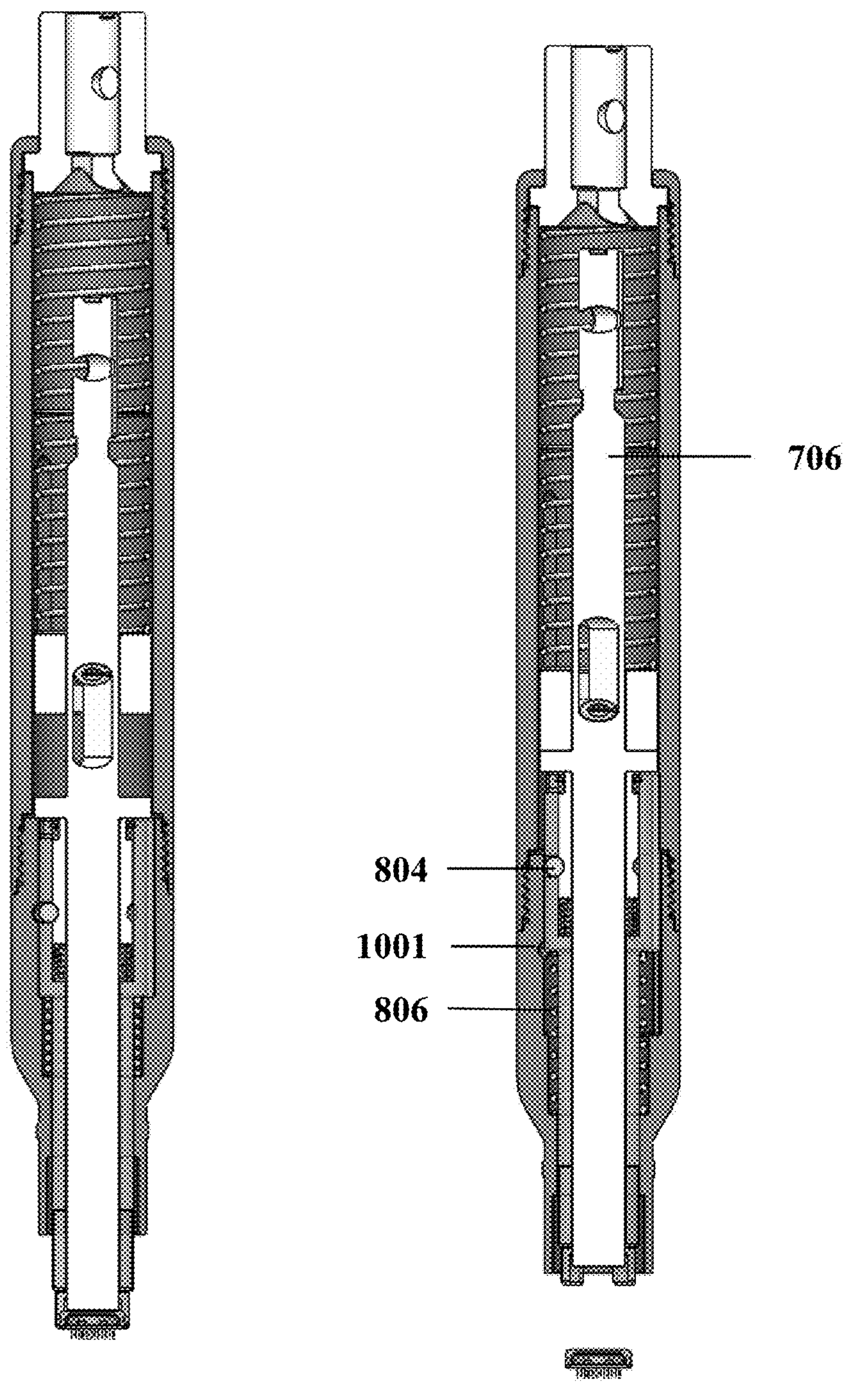
FIG. 10 illustrates motions of the retraction mechanism.

The triggering mechanism can be configured to activate the retraction mechanism at a predetermined position (e.g., a device state) within a duration of time elapsed between the first time and the second time. The predetermined position can be a position in which members of the device are in a specific configuration or state. The triggering mechanism can permit activation of the retraction mechanism when members of the device are in a specific configuration, state, or position. For example, the triggering mechanism may comprise ball bearings 804 that mechanically couple the implant support 207 to the housing of the device. The ball bearings 804 can lock the implant support 207 in a protracted position with the distal end of the implant support, comprising the implant, extended from the device. When members of the device are in a specific configuration, the ball bearings can change position within the device, and can unlock the housing of the device from the implant support. This unlocking can trigger activation of the retraction mechanism. This process is illustrated in, e.g., FIG. 9 and FIG. 10.

Retraction Mechanism

The device can comprise a retraction mechanism. The retraction mechanism can be configured to retract one or more parts of the device so that secondary contact can be prevented or minimized. In some embodiments, the retraction mechanism can be configured to retract the implant support after the propulsion mechanisms propels the implant support. The retraction mechanism can be configured to retract the implant support before the implant is inserted. In some embodiments, the retraction mechanism can be configured to retract the implant support before the propulsion mechanisms propels the implant support. In some embodiments, the retraction mechanism can be configured to retract the implant support after the implant is inserted.

The retraction mechanism can be configured to retract the implant support less than 10, 9, 8, 7, 6, 5, 4, 3, 2, or 1 ms before the implant is inserted. The retraction mechanism can be configured to retract the implant support more than 0, 1, 2, 3, 4, 5, 6, 7, 8, or 9 ms before the implant is inserted. The retraction mechanism can be configured to retract the implant support when the implant is less than 5, 4, 3, 2, or 1 mm from the tissue. The retraction mechanism can be configured to retract the implant support when the implant is more than 0, 1, 2, 3, or 4 mm from the tissue.

Implant Support

The device can further comprise an implant support. The implant support can be in mechanical communication with the implant. The implant support can comprise a gripping mechanism. The gripping mechanism can grip the implant. The gripping mechanism can comprise a collet. The collet can comprise one or more flexure prongs. The collet can be configured to grip the implant when in a first state. The flexure prongs of the collet can grip the implant when the device is in the first state. The collet can be protracted from a distal end of the device when in the first state.

The collet can comprise a second state where the collet does not grip the implant. The flexure prongs of the collet may not grip the implant in the second state. The collet can retract into the device in the second state. The propulsion mechanism can contact flexure prongs of the collet after firing, thereby opening the flexure prongs and releasing the implant.

Implants

The implant can comprise a plurality of electrodes. The plurality of electrodes can comprise a plurality of electrical contact regions. The electrical contact regions can be areas of low electrical impedance. The electrical contacts can be areas of high electrical charge conductance. In some embodiments, the electrodes are insulated outside of the contact regions. In some embodiments, the electrodes are made of a nonconductive material outside of the contact region. In some embodiments, the electrodes can be wire electrodes. In some specific embodiments, the electrodes can be tungsten electrodes. In some specific embodiments, the electrodes can be platinum iridium electrodes. An electrode can have a contact region at the distal tip of the electrode. An electrode can have a contact region on a lateral surface of the electrode. An electrode can comprise one contact region or a plurality of contact regions. The plurality of electrodes can each comprise a contact region in the plurality of contact regions. The plurality of contact regions can comprise at least 2, 5, 10, 20, 50, 100, 500, or 1000 contacts. The plurality of contact regions can comprise at most 2, 5, 10, 20, 50, 100, 500, or 1000 contacts. The plurality of contact regions can comprise a density of 1 to 25, 2 to 20, or 4 to 16 contacts per square millimeter.

Methods

In some aspects, the present disclosure provides a method for inserting an implant into a tissue of a subject. A device configured to propel the implant from the device can be provided. The device can be aimed at a target area of the tissue of the subject. Upon firing the device, the implant can be propelled to the target area. The device can be configured to activate a retraction mechanism when the implant is propelled from 35% to 75% of a total travel distance to a target area. As the implant travels, the retraction mechanism can be activated. The retraction mechanism can prevent or substantially reduce the risk of double tapping or contacting the tissue with the device after the implant has already been inserted. The implant can be inserted from 0.5 mm to 3.0 mm into the tissue of the subject. The implant can be inserted at least 0.1, 0.3, 0.5, 1, 2, 3, 4, 5, 6, 7, 8, 9, or 10 mm into the tissue of the subject. The implant can be inserted at most 0.1, 0.3, 0.5, 1, 2, 3, 4, 5, 6, 7, 8, 9, or 10 mm into the tissue of the subject.

The device can be aimed, fired, or both at various angles or orientations without risk of the implant falling off from the device or from the target area of the tissue of the subject prior to firing. The implant can be secured to the device, e.g., via an implant support. For example, FIG. 4 shows an instance where the implant is to be inserted at multiple different angles. The device can be fired upwards, downwards, or sideways. The angle can be at least 0, 5, 10, 15, 30, 60, 90, 120, 150, 165, 170, or 175 degrees offset from the direction of gravity. The angle can be at most 5, 10, 15, 30, 60, 90, 120, 150, 165, 170, 175, or 180 degrees offset from the direction of gravity.

The device can be aimed, fired, or both a various distances from the target area of the tissue of the subject. A distal end of the device can be placed next to the tissue of the subject. The distal end of the device can be placed in contact with the tissue. The distal end of the device can be placed with a gap between the tissue and the distal end. The implant may travel a total distance of from 2 mm to 4 mm, or about 2.9 mm. The implant may travel a total distance of at least 1, 2, 3, 4, 5, 6, 7, 8, 9, or 10 mm. The implant may travel a total distance of at most 1, 2, 3, 4, 5, 6, 7, 8, 9, or 10 mm.

In some embodiments, inserting an implant comprises inserting the electrodes of the implant into a tissue of the central nervous system. The electrodes can be entirely or partially inserted into the tissue of the central nervous system. In some embodiments, an inserted implant can comprise electrodes that are not inserted (entirely or partially) in the central nervous system. A plurality of contact regions of an inserted implant can be entirely or partially inserted into the tissue. In some embodiments, a plurality of contact regions of an inserted implant are not inserted (entirely or partially) in the central nervous system.

Neural Tissue

In some aspects, the present disclosure provides methods for inserting an implant into a tissue in the central nervous system. In some embodiments, the implant comprises an electrode array. Non-limiting examples of tissues in the central nervous system include tissues in the brain and tissues in the spinal cord. In some embodiments, the implant is inserted into the brain. In some embodiments, the implant is inserted into the spinal cord.

In some aspects, the present disclosure provides methods of inserting an implant into a neural tissue in the central nervous system. In some embodiments, the neural tissue comprises a neuronal tissue (e.g., a tissue comprising neurons). In some embodiments, the neural tissue comprises a tissue comprising glial cells (e.g., astrocytes, oligodendrocytes or Schwann cells). The neural tissue can comprise neuronal projections (e.g., axons). In some embodiments, the neural tissue can comprise a part of the brain. In some embodiments, the neural tissue comprises a part of the spinal cord.

In some embodiments provided herein are methods of inserting an electrode array implant into (e.g., having the contacts of electrodes inserted into) the cerebral cortex (e.g., the neocortex). The implant can be inserted into the frontal lobe, the parietal lobe, the occipital lobe, or the temporal lobe. The implant can be inserted into two or more lobes of the brain. For example, part of the implant may be inserted in the front lobe and part of the implant may be inserted in the parietal lobe. The implant can be inserted into a cortical area of the brain. A cortical area into which electrodes are implanted by the insertion device can comprise a motor cortical area, a somatosensory cortical area, a visual cortical area, an auditory cortical area, an olfactory cortical area, a gustatory cortical area, or a multi-sensory cortical area. A cortical area into which electrodes are inserted can be a cortical area associated with cognition, e.g., the prefrontal area. The cortical area can comprise one of more of the premotor cortex, the primary motor cortex, the secondary motor cortex, the primary somatosensory cortex, the secondary somatosensory cortex, the prefrontal cortex, the primary auditory cortex, the secondary auditory cortex (the auditory association area), the primary visual cortex, the secondary visual cortex (the visual association area), the primary olfactory cortex, the primary gustatory cortex, Wernicke's area, Broca's area or a combination of cortical areas. For example, the implant can have electrodes in both the primary motor cortex and the primary somatosensory cortex.

The electrodes of the electrode array can comprise electrical contacts. In some embodiments, the electrical contact of an electrode can be on the distal tip of a wire electrode. The electrode array implant inserter device may insert the tips of the electrodes each comprising an electrical contact into one or more cortical layers. In some embodiments described herein, using the electrode array implant inserter device, the tips of the electrodes can be inserted into cortical layer I, layer II, layer III, layer IV, layer V, layer VI, or a combination of cortical layers.

In some aspects, a method provided herein can be used to insert an electrode array implant into an area of the central nervous system that does not comprise the cerebral cortex. In some embodiments, the electrode array can be inserted into a cerebellum. In some embodiments, the electrode array can be inserted into a spinal cord. In some embodiments, the electrode array can be inserted into a brain stem.

Figure 15:
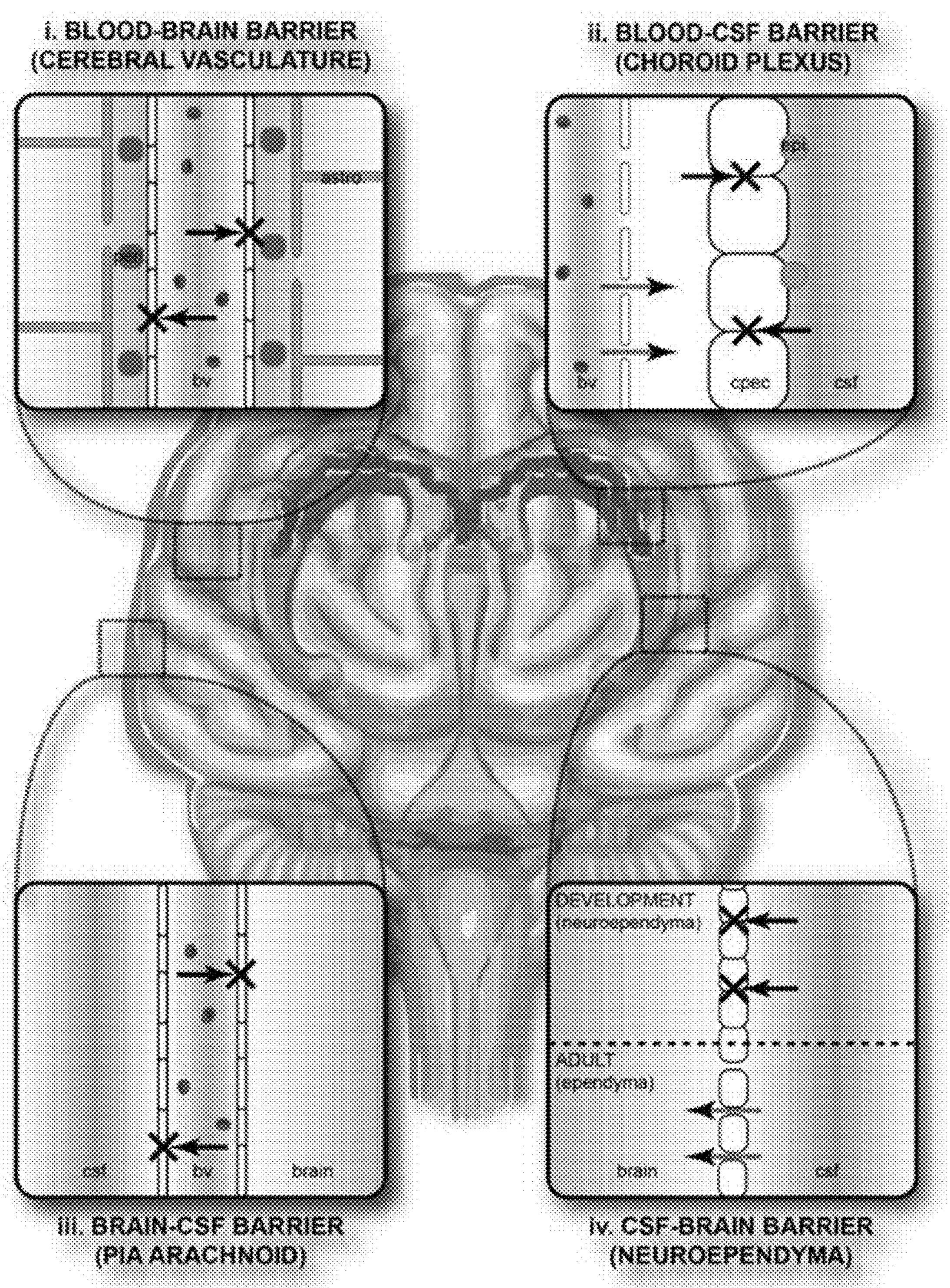
FIG. 15 provides an illustration of tissues in the central nervous system. H. B. Stolp, S. A. Liddelow, I. Sá-Pereira, K. Dziegielewska, and N. Saunders. *Front. Integr. Neurosci.*, 23 Aug. 2013 @ 2013 (CC BY).
Figure 16:
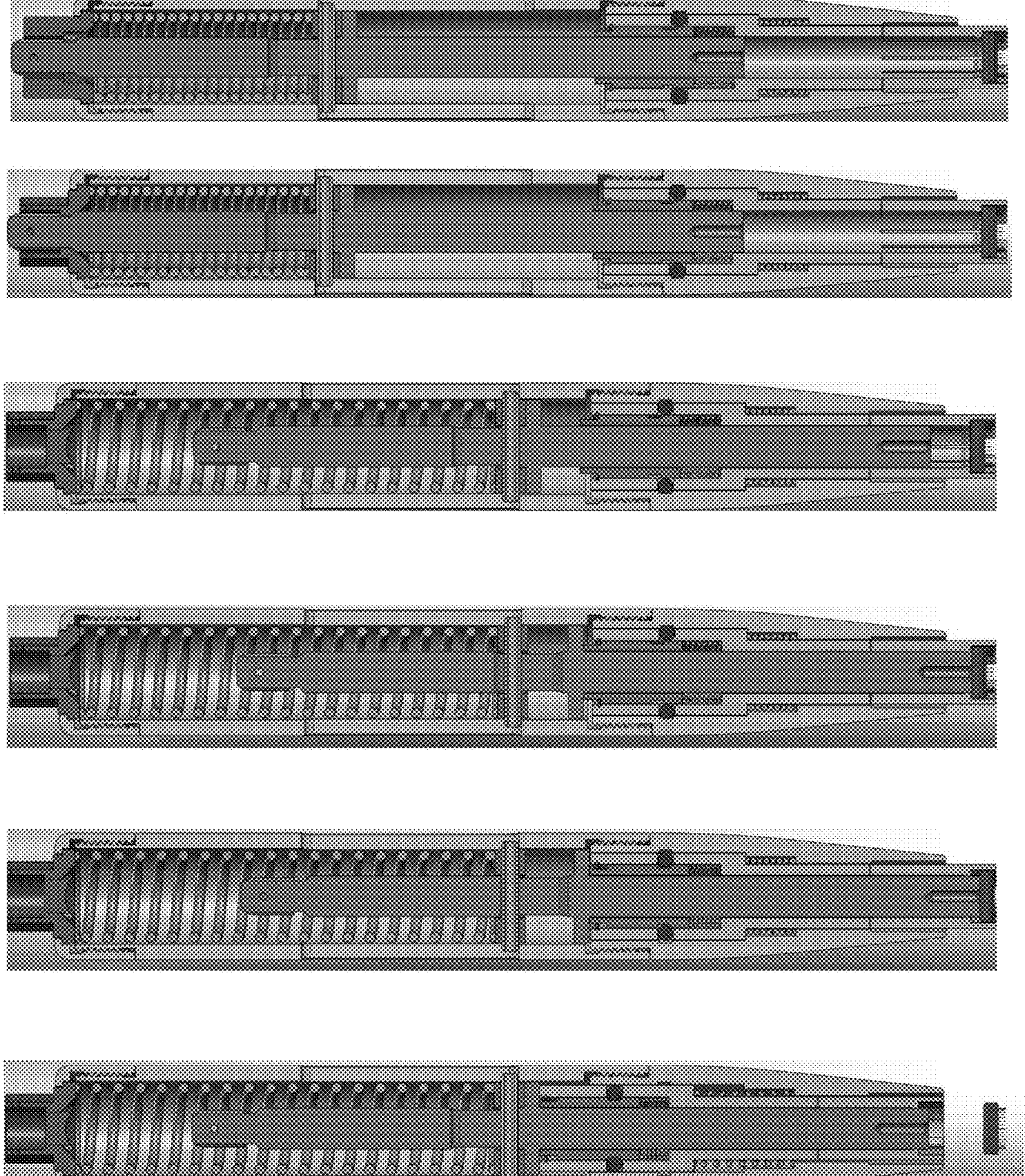
FIG. 16 provides illustrates motions of the mechanisms of an embodiment of a device.

In some embodiments, the implant inserter device can insert a part of the electrode array (e.g., a plurality of electrodes) into a tissue in the central nervous system that is not a neural tissue. In some embodiments, a part of the electrode array can be inserted into an epithelial tissue, a connective tissue, a vascular tissue, or any combination thereof. In some specific embodiments, a part of the electrode array can be inserted into a meningeal tissue. In some even more specific embodiments, a part of the electrode array can be inserted into a pia mater, a dura mater, an arachnoid mater, or any combination thereof. In some specific embodiments, a part of the electrode array can be inserted into a blood vessel. In some specific embodiments, a part of the electrode array can be inserted into a blood-brain barrier tissue. Illustrations of tissues into which the electrode array can be inserted (in part or in full) are provided in FIG. 15 (H. B. Stolp, S. A. Liddelow, I. Sá-Pereira, K. Dziegielewska, and N. Saunders. *Front. Integr. Neurosci.*, 23 Aug. 2013 @ 2013 (CC BY)).

In some embodiments, the present disclosure provides a method of inserting an electrode array implant into a neural tissue in the central nervous system of a mammal. The mammal can be a bovine, an ungulate, a rodent, a canine, a feline, or a primate. In some embodiments, the electrode array implant is inserted into a neural tissue in the central nervous system of a bovine. In some embodiments, the electrode array implant is inserted into a neural tissue in the central nervous system of an ungulate. In some embodiments, the electrode array implant is inserted into a neural tissue in the central nervous system of a rodent. In some embodiments, the electrode array implant is inserted into a neural tissue in the central nervous system of a canine. In some embodiments, the electrode array implant is inserted into a neural tissue in the central nervous system of a feline. In some embodiments, the electrode array implant is inserted into a neural tissue in the central nervous system of a primate. In some specific embodiments, the electrode array implant is inserted into a neural tissue in the central nervous system of a macaque. In some specific embodiments, the electrode array implant is inserted into a neural tissue in the central nervous system of a human.

In some embodiments, a plurality of contact areas of an inserted implant are in contact (e.g., electrical contact or mechanical contact) with a tissue in the central nervous system. In some embodiments, a plurality of contact areas of an inserted implant are in contact with a tissue in the brain. In some embodiments, a plurality of contact areas of an inserted implant are in contact with a tissue in the spinal cord. In some embodiments, a plurality of contact areas of an inserted implant are in contact with a neural tissue. In some embodiments, a plurality of contact areas of an inserted implant are in contact with a cerebral cortical area of the brain. The electrodes of an inserted implant can be used to measure electrical activity in a region of the central nervous system. The electrodes of an inserted implant can be used to measure neuronal activity in a region of the central nervous system. The electrodes of an inserted implant can be used to electrically stimulate a region of the central nervous system. The electrodes of an inserted implant can be used to stimulate neuronal activity in a region of the central nervous system.

Kits

A device of the present disclosure can be provided in a kit. A kit can comprise a hermetically sealed package, wherein the hermetically sealed package comprises a device configured to insert an implant into a tissue of a central nervous system of a subject upon activation.

FIG. 3 shows a schematic of a kit. The kit can comprise 1, 2, 3, 4, 5, or any number of devices. The kit can comprise 1, 2, 3, 4, 5, or any number of implants. The devices, the implants, or both, can be provided in one package, two packages, or any number of packages.

In some aspects, the present disclosure provides a kit comprising a first package, comprising any one of the devices provided herein. The kit can comprise a hermetically sealed package, comprising an implant. The device and the implant can be configured to be assembled. In some embodiments, the device and implant may be pre-assembled. The device, the implant, or both can be pre-sterilized.

The kit can be accompanied with instructions, e.g., on a box or on a separate sheet. The kit can comprise a code for associating the device or the implant with a subject recipient of the implant. The code can comprise a barcode, a QR code, a serial number, or any code sufficient to identify the device or the implant.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: Device

This example provides schematics of an embodiment of a device, displaying its mechanisms and their functions.

Figures 5A, 5B:
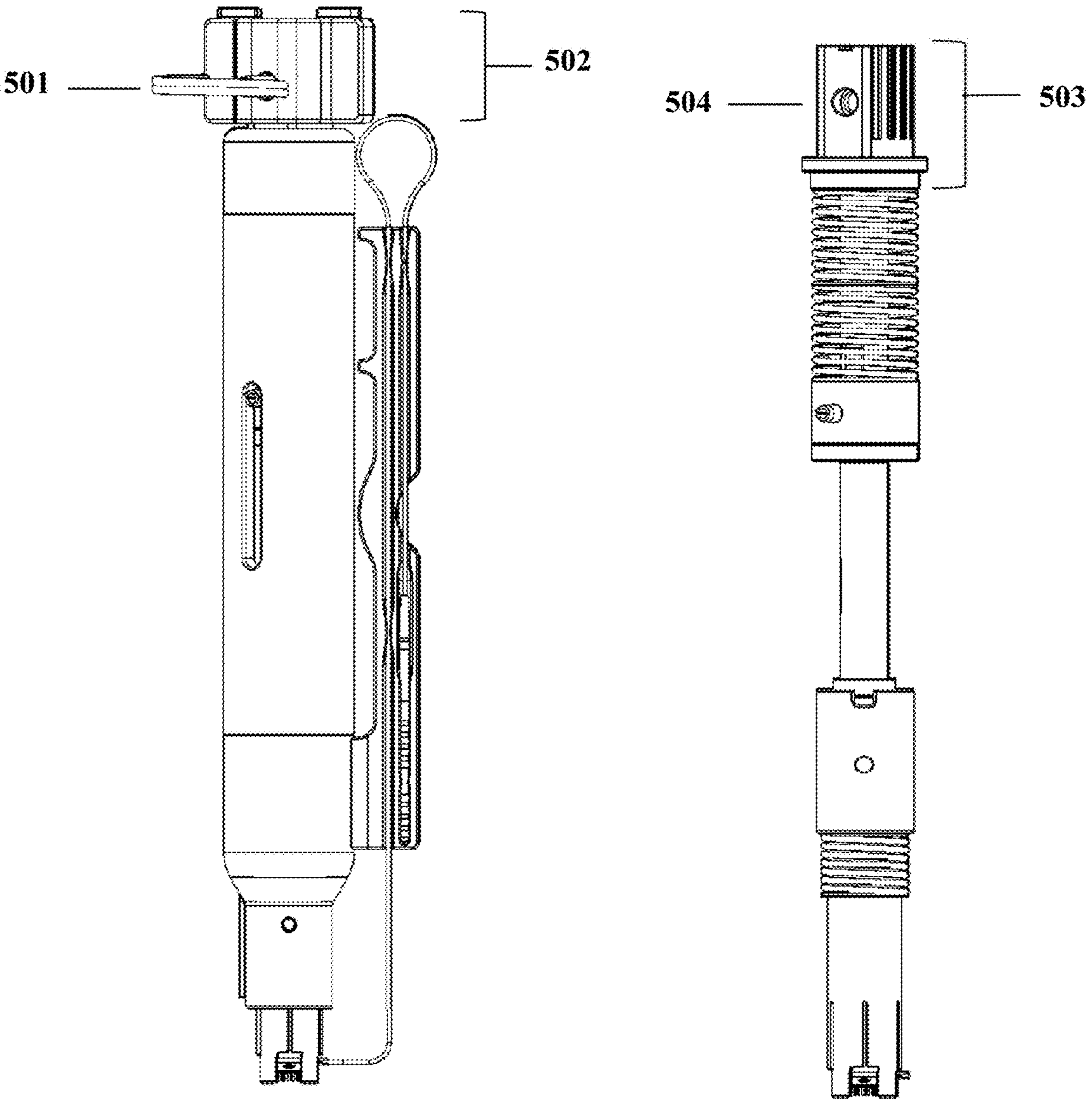
FIGS. 5A-5B provide schematics of the device with figure labels for the firing mechanism components.
Figure 6:
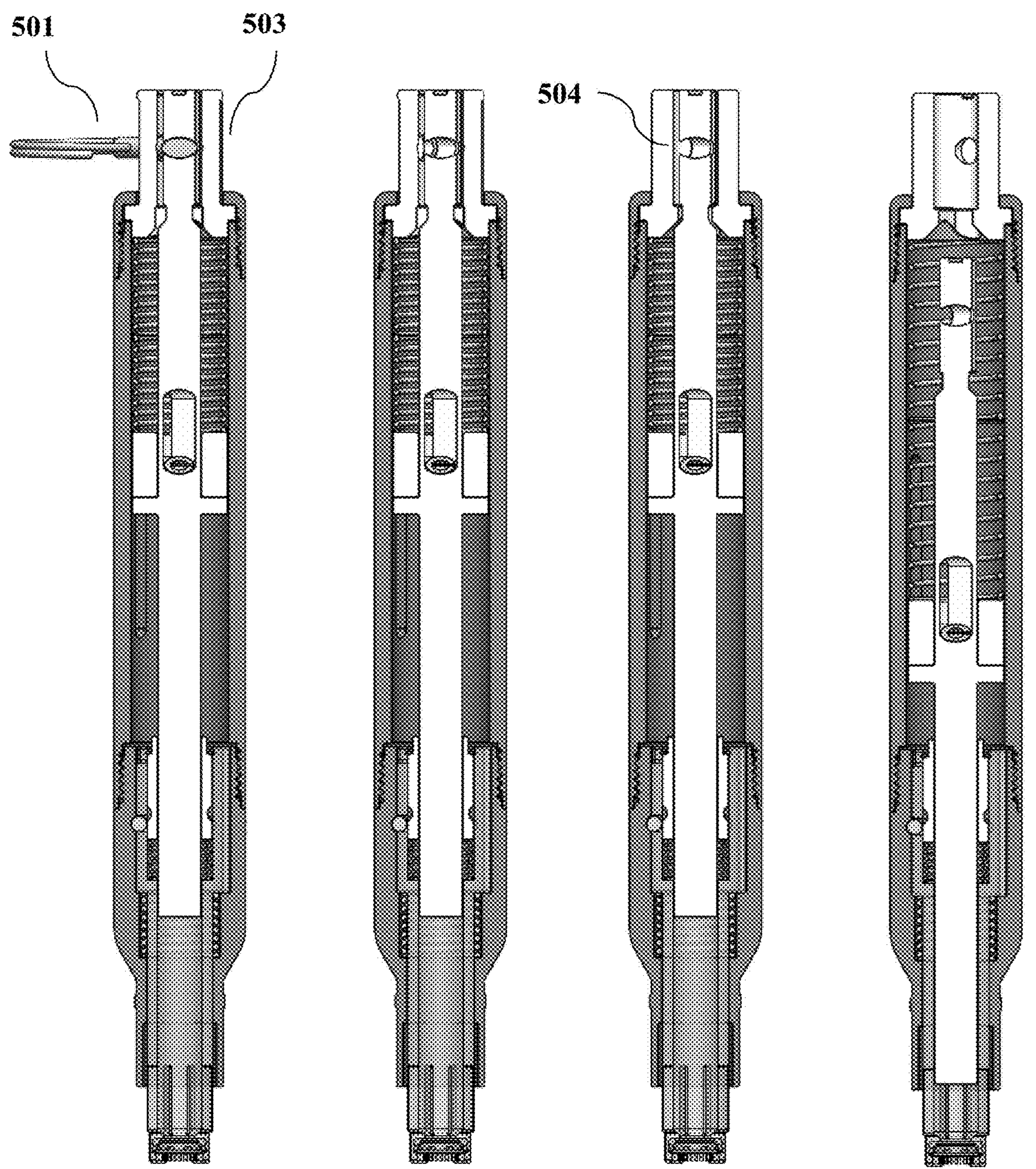
FIG. 6 illustrates motions of the firing mechanism components.

FIGS. 5A-5B provide schematics of the device with figure labels for the firing mechanism components. The firing mechanism has a ring grip quick-release pin 501 that can be pulled from the quick-release pin hole 504, which allows the firing turn key 503 disposed in a large knob 502 to release and rotate. The rotation of the firing turn key activates the propulsion mechanism. The motions of the firing mechanism components are further illustrated in FIG. 6.

Figure 7:
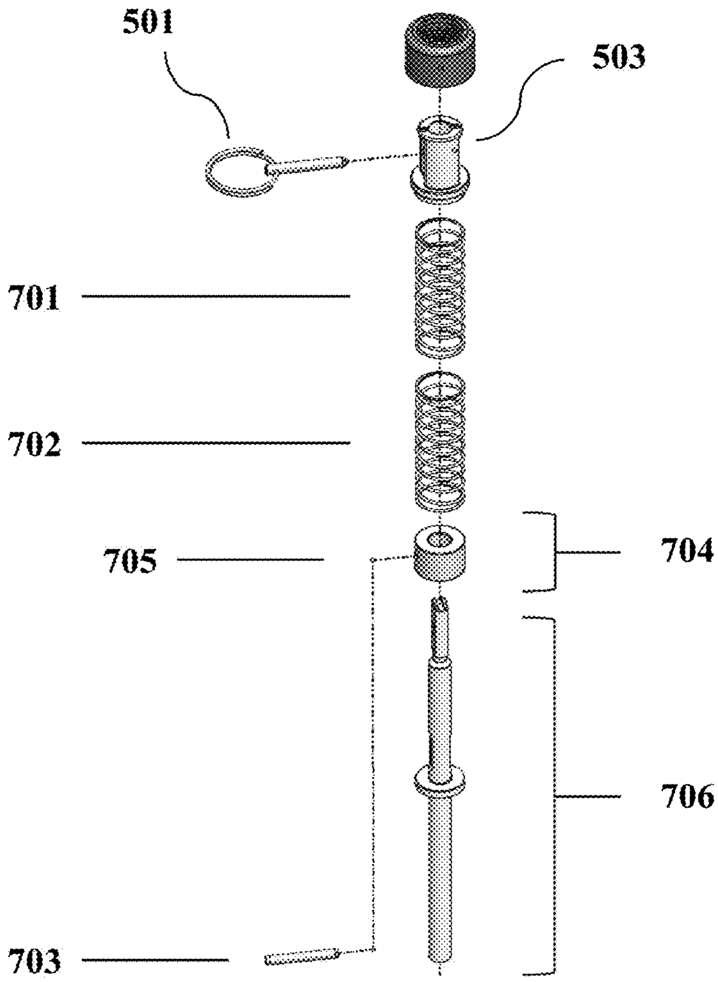
FIG. 7 provides a schematic of the propulsion mechanism.

FIG. 7 provides a schematic of the propulsion mechanism. When the propulsion mechanism is activated by the rotation of the firing turn key, the compressed springs 601, 602 extend to push on the hammer plate 604, which propels the hammer 606.

Figures 8A, 8B:
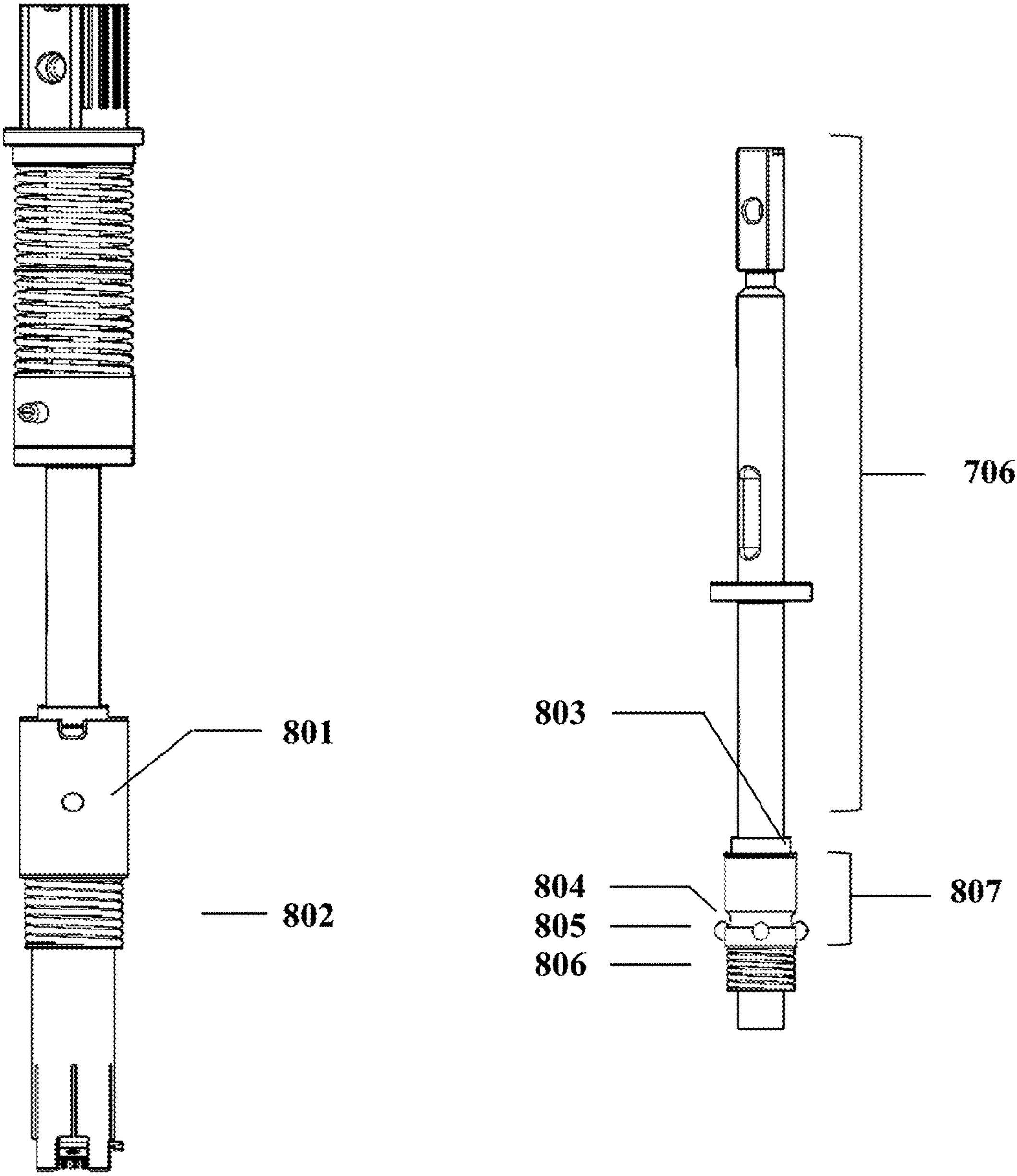
FIGS. 8A-8B provide schematics of the retraction mechanism and the triggering mechanism.
Figure 13:
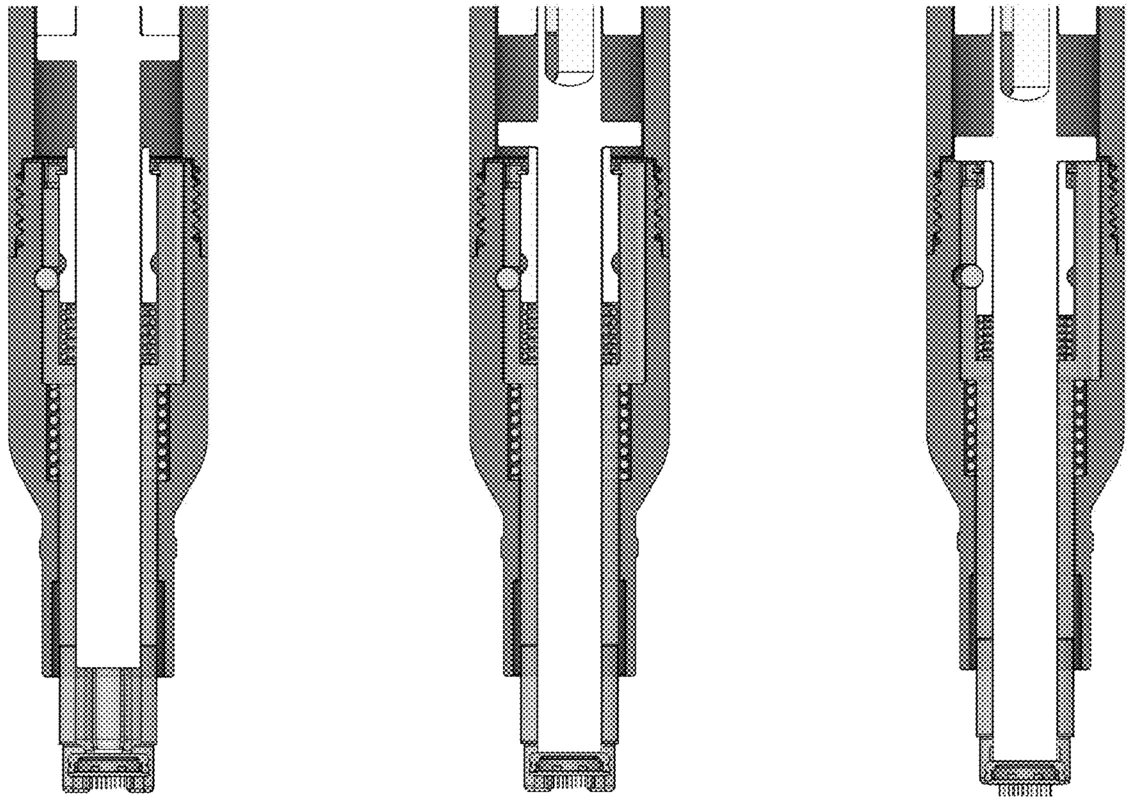
FIG. 13 provides an enlarged view of the motions of the triggering mechanism illustrated in FIG. 9.
Figure 14:
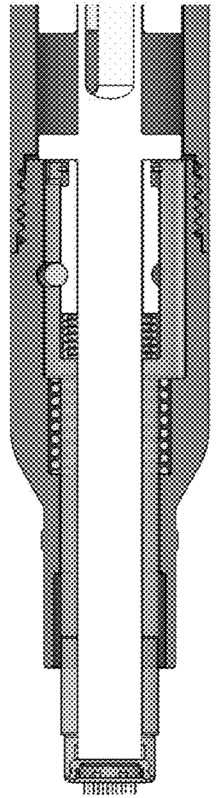
FIG. 14 provides an enlarged view of the motions of the retraction mechanism illustrated in FIG. 10.
Figure 14:
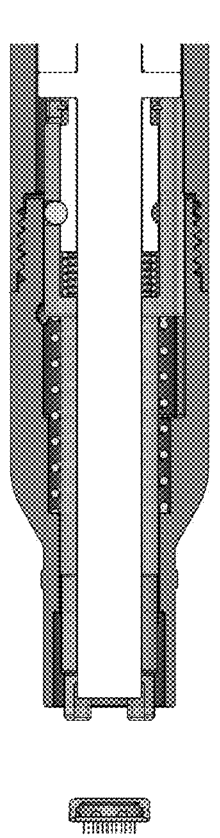

FIGS. 8A-8B provide schematics of the retraction mechanism and the triggering mechanism. The retraction mechanism has ball bearings 804 which are initially engaged with the ball bearing holes 801 in the implant support 207 and with detents in the housing of the device 1001, locking the implant support in a protracted position. When the propelled hammer 706 travels a sufficient distance, a flange on the hammer presses a ball retainer tube 807 toward the distal end of the device, which compresses a ball detent spring 806. As the ball retainer tube travels distally, ball detents 805 in the tube align with the ball bearing holes in the implant support 207. The force of the ball detent spring 806 on the implant support 207 forces the ball bearings to move from the detents in the device housing to the ball detents 805 in the ball retainer tube, unlocking the implant support 207 from the housing. The unlocking of the implant support from the housing triggers the retraction mechanism by allowing the retraction spring 802 to release, retracting the hammer 706 and the implant support 207. The motions of the propulsion mechanism that triggers the ball bearings to disengage are further illustrated in FIG. 9. The motions of the retraction mechanism that retracts the hammer are further illustrated in FIG. 10. Detailed views of the triggering and retraction mechanisms are provided in FIG. 13 and FIG. 14, respectively.

Figures 11A, 11B:
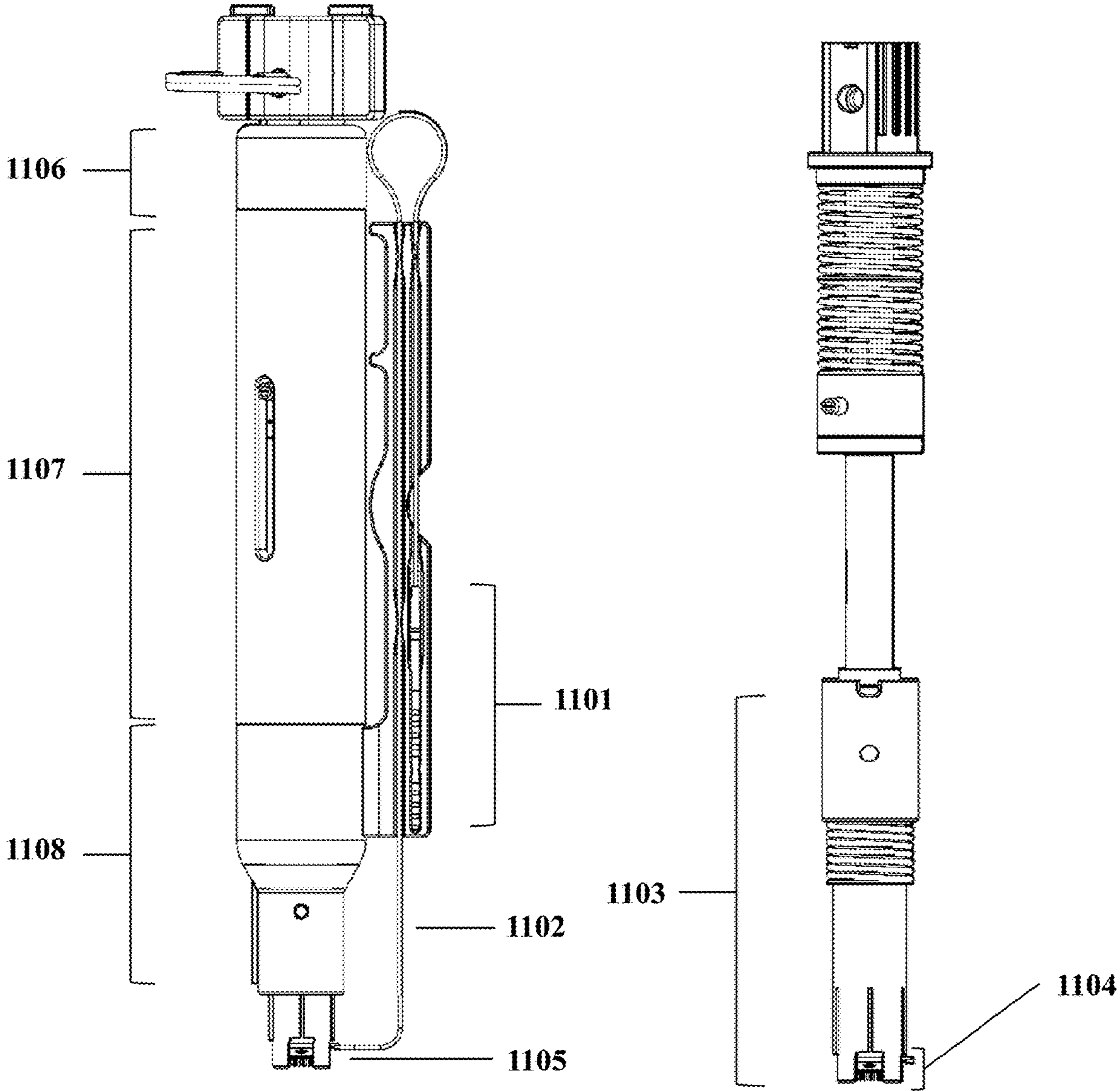
FIGS. 11A-11B provide schematics of the device with components of the housing and the implants labeled.

FIGS. 11A-11B provide schematics of the device with components of the housing and the implants labeled. The internal mechanisms of the device are housed in several housing pieces that can be assembled. The housing includes a threaded cap 1106 and an outer sleeve for the proximal end 1107 and the distal end 1108. The implant 1105 is coupled to the device via an implant support 207. The implant support comprises an implant holder 1103. The implant support comprises a collet 1104. The collet comprises flexure prongs. The implant is engaged with the collet 1104 which is configured to expand slightly when the implant is propelled by the hammer e.g., the flexure prongs can be pressed outward by the hammer, which releases the implant from the collet. The implant wire 1102, comprising a plurality of wires configured to carry a plurality of electrical signals to or from the electrodes, and the wire plug, configured to connect the electrode wire to, e.g., an amplifier or a stimulator, can be held neatly in place by a fixture in the housing.

Figures 12A, 12B:
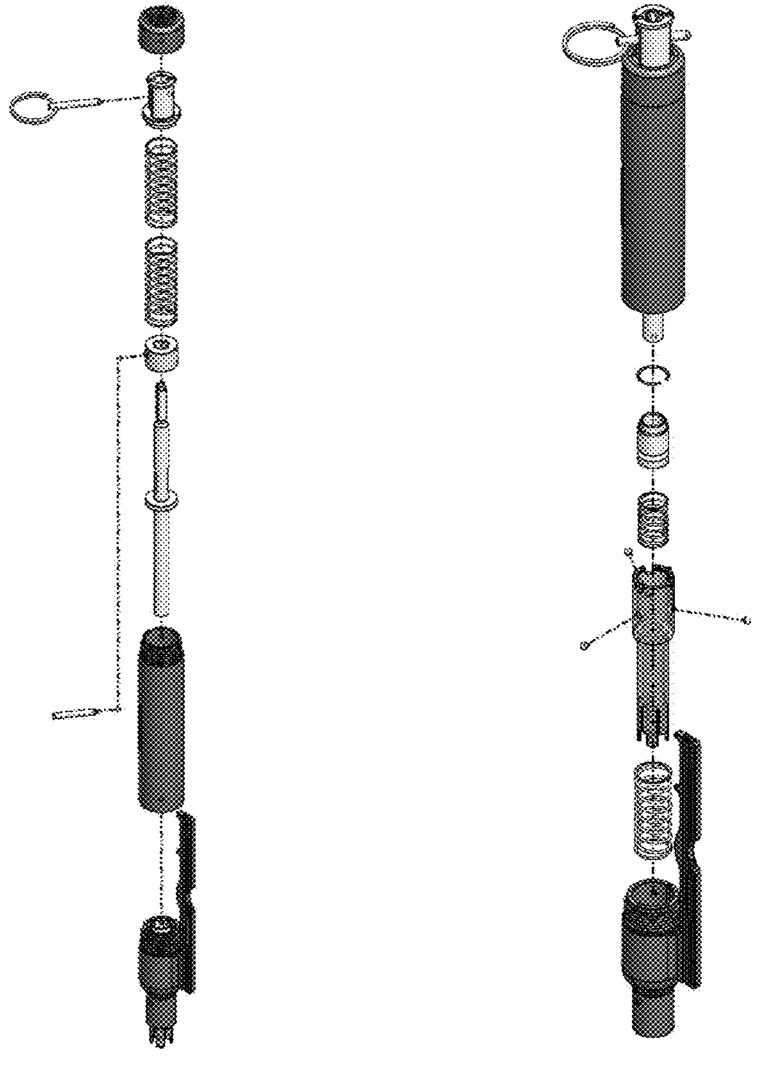
FIGS. 12A-12B provide exploded views of the device.

FIGS. 12A-12B show exploded diagrams of the device.

TABLE 1

Key map for device components and figure reference numbers.

| Component | Reference number |
|---|---|
| Ring-Grip Quick-Release Pin | 501 |
| Large Knob | 502 |
| Firing Turn Key | 503 |
| Quick-Release Pin Hole | 504 |
| Hammer Spring 1 | 701 |
| Hammer Spring 2 | 702 |
| Slotted Spring Pin | 703 |
| Hammer Plate | 704 |
| Pin Slot | 705 |
| Hammer | 706 |
| Ball Bearing Hole | 801 |
| Retraction Spring | 802 |
| Retaining Ring | 803 |
| Ball Bearing | 804 |
| Ball Detent | 805 |
| Ball Detent Spring | 806 |
| Ball Retainer Tube | 807 |
| Housing detent | 1001 |
| Implant Wire Plug | 1101 |
| Implant Wire | 1102 |
| Implant Holder | 1103 |
| Collet | 1104 |
| Implant | 1105 |
| Threaded Cap | 1106 |
| Outer Sleeve Proximal End | 1107 |
| Outer Sleeve Distal End | 1108 |

Example 2: Method

This example provides a method of use of the electrode array implant inserter device.

Prior to surgery, images of the subject's brain will be obtained. The images may be obtained using an x-ray (e.g., a computed tomography scan, CT scan) machine, a functional magnetic resonance imaging (fMRI) machine, or by another method. These images will be used to stereotactically guide the insertion of the implant array. Additional methods can be used to guide the implantation of the device, for example anatomical knowledge of the brain (e.g., a brain atlas.) The insertion angle and insertion path of the implant will be planned prior to surgery.

The subject (e.g., a human subject) will be anesthetized prior to surgery. The subject can receive a general anesthetic or a local anesthetic. The hair on the subject's head will be shortened or removed in preparation for surgery. The subject's cranium will be stereotactically fixed using a stereotactic device. The subject's scalp will then be sterilized, and an incision will be made in the scalp to expose the cranium above the area of the brain into which the implant will be inserted. A craniotomy will then be performed to remove the cranium over the area of the brain into which the implant will be inserted. Finally, the dura mater covering the brain area where the implant will be inserted will be removed (durectomy). The arachnoid layer and the pia mater will remain largely undisturbed.

The sterile packaging of electrode array implant inserter device will be opened (FIG. 3) and the sterile electrode array implant inserter device will be removed. In some cases, the device will comprise the electrode array implant 1105, and in other cases, the implant 1105 will be provided separately and will be inserted into the implant holder 1103 in the proper orientation. Optionally, the electrode array implant inserter device may then be mounted in the stereotactic device in which the subject's cranium is fixed (e.g., the inserter device will be mounted in a stereotactic arm). The implant wire 1102 will then be connected to a recording device (e.g., a device comprising an amplifier) or a stimulating device using the implant wire plug 1101. The implant inserter device will be positioned (e.g., manually or stereotactically using a manipulator) at the desired local above the subject's brain. The distal end of the device will be approximately 1 mm above the exposed meningeal tissue of the brain. Depending on the desired implantation site or other factors, the device will or will not be held perpendicular to the surface of the brain (FIG. 4).

The ring-grip quick-release pin 501 will then be removed from the device, and the firing turn key 503 will be turned. The turning of the firing turn key 503 will lead to the implant 1105 being propelled from the device into the tissue of the central nervous system. A plurality of contact regions of the electrode array will travel through the pia mater and implant in the brain of the subject. At this point, using the electrode array implant, it will be possible to begin measuring neural activity in or begin stimulating (delivering electrical current to) the neuronal tissue into which the electrode contacts are implanted.

The electrode contact sites will be implanted in a cortical area of the brain. The cortical area of the brain may be, for example, the primary motor cortex, the premotor cortex, primary somatosensory cortex, the secondary somatosensory cortex, or the prefrontal cortex. The contacts of the electrode array will be implanted at a depth of approximately −1 mm (e.g., in the meningeal tissue) to 3 mm from the surface of the brain.

Optionally, more than one implant will be inserted in the brain during a surgery (FIG. 1). If more than one implant will be inserted, the craniotomy will be made larger than if a single array is to be inserted, or more than one craniotomy will be performed. If multiple arrays are inserted, the arrays may be inserted into the same brain area or into different brain areas. The arrays may be inserted sequentially or at the same time.

The position of the implant will be fixed in the central nervous system, the craniotomy will be covered, and the scalp will be sutured. The patient will recover from anesthesia and post-operative care will be provided.

Although the description has been described with respect to particular embodiments thereof, these particular embodiments are merely illustrative, and not restrictive. Concepts illustrated in the examples may be applied to other examples and implementations.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A device for inserting an implant into a tissue in the central nervous system of a subject, comprising:

(a) an implant support configured to be in mechanical communication with the implant;

(b) a propulsion mechanism configured to propel the implant towards the tissue at a first time; and (c) a triggering mechanism configured to activate a retraction mechanism at a second time, wherein the retraction mechanism is configured to retract the implant support upon activation, wherein a duration of time elapsed between the first time and the second time is less than about 200 milliseconds.

2. The device of claim 1, wherein the propulsion mechanism comprises an internal energy source configured to propel the implant towards the tissue, wherein the internal energy source is within a sterile field of the device.

3. The device of claim 2, wherein the propulsion mechanism does not require an energy source external to the sterile field of the device to propel the implant towards the tissue with a velocity sufficient to insert the implant into the tissue to a predetermined depth.

4. The device of claim 2, wherein the internal energy source is contained within a housing of the device.

5. The device of claim 2, wherein at least about 20% of a kinetic energy of the implant, when propelled, is provided from the internal energy source.

6. The device of claim 5, wherein less than 20% of the kinetic energy of the implant, when propelled, is provided from an external energy source.

7. The device of claim 6, wherein the external energy source comprises an external positive pressure source.

8. The device of claim 1, wherein the retraction mechanism is configured to begin retraction of the implant support after the propulsion mechanism propels the implant towards the tissue at the first time.

9. The device of claim 1, wherein the retraction mechanism is configured to begin retraction of the implant support before the propulsion mechanism propels the implant towards the tissue at the first time.

10. The device of claim 1, wherein the retraction mechanism is configured to retract the implant support before the implant is inserted in the tissue of the central nervous system.

11. The device of claim 1, wherein the triggering mechanism comprises ball bearings.

12. The device of claim 11, wherein the triggering mechanism actuates via a change in the position of the ball bearings within the device.

13. The device of claim 1, wherein the device is configured to avoid contacting the tissue or the implant after the implant is inserted into the tissue.

14. The device of claim 1, further comprising a firing mechanism configured to activate the propulsion mechanism.

15. The device of claim 14, wherein the firing mechanism comprises a firing turn key.

16. The device of claim 14, wherein the firing mechanism is configured to prevent rotation of the propulsion mechanism upon firing.

17. The device of claim 1, wherein the implant support comprises a gripping mechanism.

18. The device of claim 17, wherein the gripping mechanism is configured to grip the implant when the device is in a first state, and wherein the gripping mechanism is configured to not grip the implant when the device is in a second state.

19. The device of claim 1, wherein the implant support is configured to protect the implant from mechanical damage until the implant is inserted into the tissue of the subject.

20. The device of claim 1, wherein the tissue is a neural tissue.

* * * * *